US006676985B1

(12) United States Patent
Julius et al.

(10) Patent No.: US 6,676,985 B1
(45) Date of Patent: Jan. 13, 2004

(54) BOVINE LACTATION ASSOCIATED IMMUNOTROPIC PROTEIN (CD14), ENCODING GENE AND APPLICATION IN B CELL ACTIVATION

(75) Inventors: Michael H. Julius, Toronto (CA); Dominik Filipp, Woodbridge (CA); Kamel Alizadeh-Khiavi, London (CA)

(73) Assignee: The Arthritis & Autoimmunity Research Centre Foundation, Toronto (CA)

(*) Notice: Subject to any disclaimer, the term of this patent is extended or adjusted under 35 U.S.C. 154(b) by 0 days.

(21) Appl. No.: 09/313,177

(22) Filed: May 18, 1999

Related U.S. Application Data

(63) Continuation of application No. PCT/CA97/00880, filed on Nov. 18, 1997, which is a continuation-in-part of application No. 08/746,883, filed on Nov. 18, 1996, now Pat. No. 6,093,693.

(51) Int. Cl.[7] ............... A23L 1/31; A23J 1/02; A61K 38/16; A61K 38/00; C07K 1/00

(52) U.S. Cl. ............... 426/645; 426/657; 426/801; 514/8; 514/21; 530/351

(58) Field of Search ............... 514/8, 21; 530/351; 426/645, 657, 801

(56) References Cited

U.S. PATENT DOCUMENTS

| 5,543,303 A | 8/1996 | Goyert |
| 5,804,189 A | 9/1998 | Goyert |

FOREIGN PATENT DOCUMENTS

| WO | WO 95/34289 | 12/1995 |
| WO | 96 32418 | 10/1996 |
| WO | 93 19772 | 10/1998 |

OTHER PUBLICATIONS

Zhou et al PNAS (1998) 95:2492–7.*
Ikeda, A. et al., "Molecular Cloning of Bovine CD 14 Gene", Journal of Veterinary Medical Science—Nihon Juigaku Zasshi, JP, Japanese Society of Veterinary Science; vol. 59, No. 8, 1997, pp. 715–719 XP002062359 ISSN: 0916–7250; Tokyo, Japan.
Jabara, H.H. et al., "Engagement of CD 14 on Monocytes Inhibits the Synthesis of Human Lgs., including lgE", The Journal of Immunology, vol. 153, pp. 972–978, 1994.
Juan, Todd S.–C. et al., "Soluble CD 14 Truncated at Amino Acid 152 Binds Lipopolysaccharide (LPS) and Enables Cellular Responses to LPS", The Journal of Biological Chemistry, vol. 270, pp. 1382–1387, 1995.
Julius, M.H. et al., "A Colostral Protein that Induces the Growth and Differentiation of Resting B Lymphocytes", The Journal of Immunology, vol. 140, No. 5, pp. 1366–1371, Mar. 1, 1987.
Löms, Ziegler–Heitbrock, H.W. et al., "CD14 is Expressed and Functional in Human B Cells", European Journal of Immunology, vol. 24, No. 8, pp. 1937–1940, 1994.
Filipp, D. et al., "Soluable DC14 Enriched in Colostrum and Milk Induces B Cell Growth and Differentiation", Proceedings of the National Academy of Sciences, vol. 98, No. 2, pp. 603–608, 2001.
Setoguchi, M. et al., "Mouse and Human CD14 (Myeloid Cell–Specific Leucine–Rich Glycoprotein) Primary Structure Deduced from CDNA Clones", Biochimica Et Biophysica Acta. Gene Structure and Expression, vol. 1008, 1989, pp. 213–222 XP002062356 ISSN: 0167–4781, figure 3; Elsevier, Amsterdam.
Simmons, D. L. et al., "Monocyte Antigen CD14 is a Phospholipid Anchored Membrane Protein", Blood; vol. 73, No. 1, 1989, pp. 284–289 XP002062358 ISSN: 0006–4971; Philadelphia, PA, U.S.A.
Ulevitch, R. J. et al., "Receptor–Dependent Mechanisms of Cell Stimulation by Bacterial Endotoxin", Annual Review of Immunology, U.S., Annual Reviews, Inc., vol. 13, 1995, pp. 437–457 XP002071335 ISSN: 0732–0582.
Viriyakosol, et al., "The N–terminal Half of Membrane CD14 is a Functional Cellular Lipopolysaccharide Receptor", Infection and Immunity, vol. 64, pp. 653–656, 1996.
Wang Y. et al., "Detection and Identification of Soluble CD14 in Bovine Milk", Molecular Biology of The Cell, vol. 8, 1997, No. 5, p. 85A XP002062360 ISSN: 1059–1524 abstract; Bethesda, MD, U.S.A.
Yang Z. et al., "Analysis of the CD14 Receptor Associated with Bovine Alveolar Macrophages", Inflammation, vol. 20, No. 1, pp. 97–106, Feb. 1996.
Yang Z. et al., "Soluble CD14 and Lipopolysaccharide–Binding Protein from Bovine Serum Enable Bacterial Lipopolysaccharide–Mediated Cytotoxicity and Activation of Bovine Vascular Endothelial Cells in Vitro", Journal of Leukocyte Biology, U.S., Federation of American Societies for Experimental, vol. 59, No. 2, 1996, pp. 241–247 XP002062361 ISSN: 0741–5400.

* cited by examiner

Primary Examiner—Christina Chan
Assistant Examiner—Michail A Belyavskyi
(74) Attorney, Agent, or Firm—John C. Hunt

(57) ABSTRACT

A protein purified from bovine colostral whey and isolated nucleotide sequences encoding the protein is identified. The isolated bovine protein is termed Bovine Lactation Associated Immunotropic (Bo-LAIT) protein. The human homologue of Bo-LAIT protein, Hu-LAIT protein, is also described. A method of activating B cells, and particularly of activating B cells in a mammal, such as a human, in need of such activation by administering LAIT protein is described. LAIT protein can be incorporated into infant formula. LAIT protein can be administered to an infant, as by feeding to the infant such formula. LAIT protein can be incorporated as part of a vaccination, LAIT protein can be administered to a patient having a T cell immune deficiency, for example, a particular T cell dysfunction in which gp39 (CD40L) is under expressed on or totally absent from the cell surface of patient T cells. Preparation of medicaments including LAIT protein for activating B cells in a mammal in need of such activation is described. Natural or recombinant LAIT protein can be used.

8 Claims, 26 Drawing Sheets

```
  1  MERASCLLLL LLPLVHVSAT TPEPCELDDE DFRCVCNFSE PQPDWSEAFQ
              D -?--?--NN? ??-?-?

51  CVSAVEVEIH AGGENCEPFL KRVDADADPR QYADTVKALR VRRLTVGAAQ
         V----?-S ---LSL?

101  VPAQLLVGAL RVLAYSRLKE LTLEDLKITG TMPPLPLEAT GLALSSLRLR

151  NVSWATGRSW LAELQQWLKP GLKVLSIAQA HSPAFSYEQV RAFPALTSLD
     ?--- ?--GA? -G---

201  LSDNPGLGER GLMAALCPNK FPAIQNLALR NTGMETPTGV CAALAAAGVO
                                       ---S-P A-----LR--

251  PHSLDLSHNS LRATVNPSAP ROMWSSALNS LNLSFAGLEQ VPKGLPAKLR
     -Q-------? -?V?

301  VLDLSCNRLN RAPQPDELPE VDNLTLDGNP FLVPGTALPH EGSMNSGVVP
                                                  L----V

351  ACARSTLSVG VSGTLVLLQG ARGFA
     ???--
```

FIG. 2

```
Majority            A T G G A G C G C G T G C C C T G C T T G T T G C T G C T G
                                  10                  20                  30
Bovine CD14 cDNA    A T G G T G T G C G T G C C C T A C C T G C T G C T G C T G  33
Human  CD14 cDNA    A T G G A G C G C G C G T C C T G C T T G T T G C T G C T G  33
Mouse  CD14 cDNA    A T G G A G C G T G T G C T T G G C T T G T T G C T G T T G C T T  33

Majority            C T G C C G - - - C T G G T G C A C G T C T C T G C G G C C A C A
                                  40                  50                  60
Bovine CD14 cDNA    C T G C C G T C A C T G C T G C G T G T G T C T G C G G A C A C A  66
Human  CD14 cDNA    C T G C C G - - - C T G G T G C A C G T C T C T G C G A C C A C G  63
Mouse  CD14 cDNA    C T G - - - - - - - - - G T G C A C G C C T C T C C G C C C C A    57

Majority            C C A G A A C C C T G C G A G C T G G A C G A X G A A G A T T T C
                                  70                  80                  90
Bovine CD14 cDNA    A C A G A A C C C T G C G A G C T G G A C G A C G A C G A T T T C  99
Human  CD14 cDNA    C C A G A A C C T T G T G A G C T G G A C G A T G A A G A T T T C  96
Mouse  CD14 cDNA    C C A G A G C C C T G C G A G C T A G A C G A G G A A A - - - - -  86

Majority            C G T T G T G T C T G C A A C T T C T C X G A T C C G A A G C C X
                                 100                 110                 120                 130
Bovine CD14 cDNA    C G T T G T G T C T G C A A C T T C A C G G A T C C G A A G C C T  132
Human  CD14 cDNA    C G C T G C G T C T G C A A C T T C T C C G A A C C T C A G C C C  129
Mouse  CD14 cDNA    - G T T G T T C C T G C A A C T T C T C A G A T C C G A A G C C A  117

Majority            G A C T G G T C C A G C G C C T T C C A G T G T X T G G X T G C X
                                 140                 150                 160
Bovine CD14 cDNA    G A C T G G T C T A G C G C C G T T C A G T G T A T G G T T G C C  165
Human  CD14 cDNA    G A C T G G T C C G A A G C C T T C C A G T G T G T G T C T G C A  162
Mouse  CD14 cDNA    G A T T G G T C C A G C G C T T T C A A T T G T T T G G G G G C G  150

Majority            G T A G A G G T G G A G A T C X A T G C C G G C G G C C G C A G C
                                 170                 180                 190
Bovine CD14 cDNA    G T C G A G G T G G A G A T C A G T G C C G G C G G C C G C A G C  198
Human  CD14 cDNA    G T A G A G G T G G A G A T C C A T G C C G G C G G T C T C A A C  195
Mouse  CD14 cDNA    G C A G A T G T G G A A T T G T A C G G C G G C G G C C G C A G C  183

Majority            C T G G A A C A G T T T C T A A A G C G X G T C G A X X C G G A C
                                 200                 210                 220                 230
Bovine CD14 cDNA    C T G G A A C A G T T T C T C A A G G G A G C C G A - - - - - - C  225
Human  CD14 cDNA    C T A G A G C C G T T T C T A A A G C G C G T C G A T G C G G A C  228
Mouse  CD14 cDNA    C T G G A A T A C C T T C T A A A G C G T G T G G A C A C G G A A  216
```

FIG. 6 A

| | | |
|---|---|---|
| Majority | G C C G A C C C G X G G C A G T A T G C T G A C A C X A T C A A G | |
| | 240 250 260 | |
| Bovine CD14 cDNA | A C C A A C C C G A A G C A G T A T G C T G A C A C A A T C A A G | 258 |
| Human CD14 cDNA | G C C G A C C C G C G G C A G T A T G C T G A C A C G G T C A A G | 261 |
| Mouse CD14 cDNA | G C A G A T C T G G G C A G T T C A C T G A T A T T A T C A A G | 249 |

| | | |
|---|---|---|
| Majority | G C T C T G C G C G T X C G G C G G C T C A C G G T G G G X G C C | |
| | 270 280 290 | |
| Bovine CD14 cDNA | G C T C T G C G C G T T C G G C G A C T C A A G C T G G G C G C T | 291 |
| Human CD14 cDNA | G C T C T C C G C G T G C G G C G G C T C A C A G T G G G A G C C | 294 |
| Mouse CD14 cDNA | T C T C T G T C C T T A A A G C G G C T T A C G G T G C G G C C | 282 |

| | | |
|---|---|---|
| Majority | G C A C A G G T T C C T G C T C A G C T T C T G G T C G G C G C C | |
| | 300 310 320 330 | |
| Bovine CD14 cDNA | G C A C A G G T T C C T G C T C A G C T T C T G G T C G C C G T T | 324 |
| Human CD14 cDNA | G C A C A G G T T C C T G C T C A G C T A C T G G T A G G C G C C | 327 |
| Mouse CD14 cDNA | G C G C G G A T T C C T A G T C G G A T T C T A T T C G G A G C C | 315 |

| | | |
|---|---|---|
| Majority | C T G C G T G T G C T C G G G T A C T C C C G C C T C A A G G A A | |
| | 340 350 360 | |
| Bovine CD14 cDNA | C T G C G C G C G C T C G G G T A C T C T C G T C T C A A G G A A | 357 |
| Human CD14 cDNA | C T G C G T G T G C T A G C G T A C T C C C G C C T C A A G G A A | 360 |
| Mouse CD14 cDNA | C T G C G T G T G C T C G G G A T T C C G G C C T C C A G G A A | 348 |

| | | |
|---|---|---|
| Majority | C T G A C G C T T G A G G A C C T X G A G G T A A C C G G C A C C | |
| | 370 380 390 | |
| Bovine CD14 cDNA | C T G A C G C T T G A G G A C C T G G A G G T A A C C G G C C C A | 390 |
| Human CD14 cDNA | C T G A C G C T C G A G G A C C T A A A G A T A A C C G G C A C C | 393 |
| Mouse CD14 cDNA | C T G A C T C T T G A A A A T C T C G A G G T A A C C G G C A C C | 381 |

| | | |
|---|---|---|
| Majority | A C G C C X C C G C C G C C T C T G G A A G C C A C X G G A C C T | |
| | 400 410 420 | |
| Bovine CD14 cDNA | A C G C C C C C G A C G C C T C T G G A A G C C G C T G G G C C T | 423 |
| Human CD14 cDNA | A T G C C T C C G C T G C C T C T G G A A G C C A C A G G A C T T | 426 |
| Mouse CD14 cDNA | G C G C C G C C A C C G C T T C T G G A A G C C A C C G G A C C C | 414 |

| | | |
|---|---|---|
| Majority | G C X C T C A C C A X C T T G A G C C T X C G C A A C G T G T C G | |
| | 430 440 450 460 | |
| Bovine CD14 cDNA | G C G C T C A C C A C C C T C A G T C T G C G T A A C G T A T C G | 456 |
| Human CD14 cDNA | G C A C T T T C C A G C T T G C G C C T A C G C A A C G T G T C G | 459 |
| Mouse CD14 cDNA | G A T C T C A A C A T C T T G A A C C T C C G C A A C G T G T C G | 447 |

FIG. 6 B

| | | |
|---|---|---|
| Majority | TGGGCAACAGGGGGTGCCTGGCTCGCCGAACTG | |
| | 470      480      490 | |
| Bovine CD14 cDNA | TGGACAACAGGAGGTGCCTGGCTCGGCGAACTG | 489 |
| Human  CD14 cDNA | TGGGCGACAGGGCGTTCTTGGCTCGCCGAGCTG | 492 |
| Mouse  CD14 cDNA | TGGGCAACAAGGGATGCCTGGCTCGCAGAACTG | 480 |
| Majority | CAGCAGTGGCTCAAGCCTGGXCTCAAGGTACTG | |
| | 500      510      520 | |
| Bovine CD14 cDNA | CAGCAGTGGCTCAAGCCTGGGCTCAGGGTGCTG | 522 |
| Human  CD14 cDNA | CAGCAGTGGCTCAAGCCAGGCCTCAAGGTACTG | 525 |
| Mouse  CD14 cDNA | CAGCAGTGGCTAAAGCCTGGACTCAAGGTACTG | 513 |
| Majority | AGCATTGCCCAAGCACACTCGCTTGCCTTTTCC | |
| | 530      540      550      560 | |
| Bovine CD14 cDNA | AACATTGCCCAAGCACACTCGCTTGCCTTTCCG | 555 |
| Human  CD14 cDNA | AGCATTGCCCAAGCACACTCGCCTGCCTTTTCC | 558 |
| Mouse  CD14 cDNA | AGTATTGCCCAAGCACACTCACTCAACTTTTCC | 546 |
| Majority | TGCGAACAGGTCCGCGCCTTCCCGGCCCTCACC | |
| | 570      580      590 | |
| Bovine CD14 cDNA | TGCGCAGGGCTCTCCACCTTCGAGGCGCTCACC | 588 |
| Human  CD14 cDNA | TGCGAACAGGTTCGCGCCTTCCCGGCCCTTACC | 591 |
| Mouse  CD14 cDNA | TGCGAACAGGTCCGCGTCTTTCCCTGCCCTCTCC | 579 |
| Majority | ACCCTAGACCTGTCTGACAATCCTGGACTGGGC | |
| | 600      610      620 | |
| Bovine CD14 cDNA | ACCCTAGACCTGTCTGACAATCCCAGTCTGGGC | 621 |
| Human  CD14 cDNA | AGCCTAGACCTGTCTGACAATCCTGGACTGGGC | 624 |
| Mouse  CD14 cDNA | ACCTTAGACCTGTCTGACAATCCTGAATGGGC | 612 |
| Majority | GAXACGXGGACTGATGGCAGCTCTCTGTCCCCA | |
| | 630      640      650      660 | |
| Bovine CD14 cDNA | GACACG-GGGCTGATGGCAGCTCTCTGTCCGAA | 653 |
| Human  CD14 cDNA | GA-ACGCGGACTGATGGCGGCTCTCTGTCCCCA | 656 |
| Mouse  CD14 cDNA | GAGA-GAGGACTGATCTCAGCCTCTCTGTCCCT | 644 |
| Majority | CAAGTTCCCGGCCCTCCAAXATCTAGCGCTGCG | |
| | 670      680      690 | |
| Bovine CD14 cDNA | CAAGTTCCCGGCCCTCCAATATCTAGCGCTACG | 686 |
| Human  CD14 cDNA | CAAGTTCCCGGCCATCCAGAATCTAGCGCTGCG | 689 |
| Mouse  CD14 cDNA | CAAGTTCCCGACCCTCCAAGTTTTAGCGCTGCG | 677 |

FIG. 6 C

```
Majority        CAACGCGGGGATGGAGACGCCCAGCGGCGTGTG
                     700           710           720
Bovine CD14 cDNA CAACGCGGGGATGGAGACGCCGAGCGGCGTGTG 719
Human  CD14 cDNA CAACACAGGAATGGAGACGCCCACAGGCGTGTG 722
Mouse  CD14 cDNA TAACGCGGGGATGGAGACGCCCAGCGGCGTGTG 710

Majority        CGCXGCGCTGGCGGCAGCAAGGGTGCAGCCCA
                     730           740           750
Bovine CD14 cDNA CGCGGCGCTGGCGGCAGCGAGGGTGCAGCCCA 752
Human  CD14 cDNA CGCCGCACTGGCGGCAGCGGCAGGTGCAGCCCA 755
Mouse  CD14 cDNA CTCTGCGCTGGCCGCAGCAAGGGTACAGCTGCA 743

Majority        AAGCCTAGACCTCAGCCACAACTCGCTGCGCGX
                     760           770           780           790
Bovine CD14 cDNA AAGCCTGGACCTCAGCCACAACTCGCTGCGCGT 785
Human  CD14 cDNA CAGCCTAGACCTCAGCCACAACTCGCTGCGCGT 788
Mouse  CD14 cDNA AGGACTAGACCTTAGTCACAATTCACTGCGGGA 776

Majority        CACCGCA--CCCXGGCGCTCCGAGATGTGTCTG
                     800           810           820
Bovine CD14 cDNA CACCGC---CCCGGGTGCTACCCGATGTGTCTG 815
Human  CD14 cDNA CACCGTAAACCCTAGCGCTCCGAGATGCATGTG 821
Mouse  CD14 cDNA TGCTGCA------GGCGCTCCGAGTTGTGACTG 803

Majority        GCCCAGTGCXCTAAACTCXCTCAATCTGTCGTT
                     830           840           850
Bovine CD14 cDNA GCCCAGTGCACTAAGGTCTCTCAATTTGTCGTT 848
Human  CD14 cDNA GTCCAGCGCCCTGAACTCCCTCAATCTGTCGTT 854
Mouse  CD14 cDNA GCCCAGTCAGCTAAACTCGCTCAATCTGTCTTT 836

Majority        CGCTGGGCTGGAGCAGGTGCCTAAAGGACTGCC
                     860           870           880           890
Bovine CD14 cDNA CGCTGGGCTGGAGCAAGTGCCTAAGGGACTGCC 881
Human  CD14 cDNA CGCTGGGCTGGAACAGGTGCCTAAAGGACTGCC 887
Mouse  CD14 cDNA CACTGGGCTGAAGCAGGTACCTAAAGGGCTGCC 869

Majority        AGCCAAGCTCAGCGTGCTXGATCTCAGCTGCAA
                     900           910           920
Bovine CD14 cDNA CCCTAAGCTCAGCGTGCTTGATCTCAGCTGCAA 914
Human  CD14 cDNA AGCCAAGCTCAGAGTGCTCGATCTCAGCTGCAA 920
Mouse  CD14 cDNA AGCCAAGCTCAGCGTGCTGGATCTCAGTTACAA 902
```

FIG. 6 D

```
Majority        CAGGCTGAACAGGGAGCCGCGGCCAGACGAGCT
                        930        940         950
Bovine CD14 cDNA CAAGCTAAGCAGGGAGCCGCGGCGAGACGAGCT  947
Human  CD14 cDNA CAGACTGAACAGGGCGCCGCAGCCTGACGAGCT  953
Mouse  CD14 cDNA CAGGCTGGATAGGAACCCTAGCCAGATGAGCT   935

Majority        GCCCGAGGTGGATAACCTGACACTGGACGGAAA
                        960        970         980          990
Bovine CD14 cDNA GCCCGAGGTAAATGACCTGACTCTGGACGGAAA  980
Human  CD14 cDNA GCCCGAGGTGGATAACCTGACACTGGACGGAA   986
Mouse  CD14 cDNA GCCCCAAGTGGGGAACCTGTCACTTAAAGGAAA  968

Majority        TCCCTTTCTGGACCCTGGAXCXXTCCXXCXCCA
                        1000       1010        1020
Bovine CD14 cDNA TCCCTTTCTGGACCCTGGAGCCCTCCAGCACCA  1013
Human  CD14 cDNA TCCCTTCCTGGTCCCTGGAACTGCCCTCCCCCA  1019
Mouse  CD14 cDNA TCCCTTTTTGGACTCTGAA----TCCCAC-TCG   996

Majority        XAAXGGCTCAATGAXCTCCGGCGTGGTCCCAGC
                        1030       1040        1050
Bovine CD14 cDNA AAATGACCCGATGATCTCCGGCGTGGTCCCAGC  1046
Human  CD14 cDNA CGAGGGCTCAATGAACTCCGGCGTGGTCCCAGC  1052
Mouse  CD14 cDNA GAGAAGTTTAA----CTCTGGCGTAGTACCGC   1025

Majority        CTGTGCXCGTTCXXXCCCTGXCXGTGGGGGTGTC
                        1060       1070        1080
Bovine CD14 cDNA CTGTGCGCGTTCTGCCTTGACCATGGGGGTGTC  1079
Human  CD14 cDNA CTGTGCACGTTCGACCCTGTCGGTGGGGGTGTC  1085
Mouse  CD14 cDNA CGGAGCTCCATCATCCCAAGCAGTGGCCTTGTC  1058

Majority        AGGAACCCTGGCGCTGCTCCAAGGAGCCCGXGG
                        1090       1100        1110         1120
Bovine CD14 cDNA AGGAGCCCTGGCGCTGCTTCAAGGAGCCCGAGG  1112
Human  CD14 cDNA GGGAACCCTGGTGCTGCTCCAAGGGGCCCGGGG  1118
Mouse  CD14 cDNA AGGAACTCTGGCTTTGCTCCTAGGAATCGCCT   1091

Majority        CTTTGCXTAA
                        1130
Bovine CD14 cDNA CTTCGCGTAA    1122
Human  CD14 cDNA CTTTGCCTAA    1128
Mouse  CD14 cDNA CTTTGTTTAA    1101
```

FIG. 6 E

| | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| Majority | M | E | R | V | X | X | L | L | L | L | L | L | P | - | L | V | H | V | S | A | X | T | P | E | P | C | E | L | D | D | E | D | F | R | C |

| | Sequence | |
|---|---|---|
| Bovine CD14 | M V C V P Y L L L L L L P S L L R V S A D T T E P C E L D D D D F R C | 35 |
| Human CD14 | M E R A S C L L L L L L P - L V H V S A T T P E P C E L D D E D F R C | 34 |
| Mouse CD14 | M E R V L G L L L L L L - - - V H A S P A P P E P C E L D E E S - - C | 30 |

Majority: V C N F S D P K P D W S S A F Q C X X A V E V E I X A G G R S L E X F

| | Sequence | |
|---|---|---|
| Bovine CD14 | V C N F T D P K P D W S S A V Q C M V A V E V E I S A G G R S L E Q F | 70 |
| Human CD14 | V C N F S E P Q P D W S E A F Q C V S A V E V E I H A G G L N L E P F | 69 |
| Mouse CD14 | S C N F S D P K P D W S S A F N C L G A A D V E L Y G G R S L E Y L | 65 |

Majority: L K R V D A D A D P X Q Y A D T I K A L R V R R L T V G A A Q V P A Q

| | Sequence | |
|---|---|---|
| Bovine CD14 | L K - - G A D T N P K Q Y A D T I K A L R V R R L K L G A A Q V P A Q | 103 |
| Human CD14 | L K R V D A D A D P R Q Y A D T V K A L R V R R L T V G A A Q V P A Q | 104 |
| Mouse CD14 | L K R V D T E A D L G Q F T D I I K S L S L K R L T V R A A R I P S R | 100 |

Majority: L L V G A L R V L G Y S R L K E L T L E D L E V T G T X P P X P L E A

| | Sequence | |
|---|---|---|
| Bovine CD14 | L L V A V L R A L G Y S R L K E L T L E D L E V T G P T P P T P L E A | 138 |
| Human CD14 | L L V G A L R V L A Y S R L K E L T L E D L K I T G T M P P L P L E A | 139 |
| Mouse CD14 | I L F G A L R V L G I S G L Q E L T L E N L E V T G T A P P P L L E A | 135 |

Majority: T G P A L X X L X L R N V S W A T G X A W L A E L Q Q W L K P G L K V

| | Sequence | |
|---|---|---|
| Bovine CD14 | A G P A L T T L S L R N V S W T T G G A W L G E L Q Q W L K P G L R V | 173 |
| Human CD14 | T G L A L S S L R L R N V S W A T G R S W L A E L Q Q W L K P G L K V | 174 |
| Mouse CD14 | T G P D L N I L N L R N V S W A T R D A W L A E L Q Q W L K P G L K V | 170 |

Majority: L S I A Q A H S L A F S C E Q V R X F P A L T T L D L S D N P X L G E

| | Sequence | |
|---|---|---|
| Bovine CD14 | L N I A Q A H S L A F P C A G L S T F E A L T T L D L S D N P S L G D | 208 |
| Human CD14 | L S I A Q A H S P A F S Y E Q V R A F P A L T S L D L S D N P G L G E | 209 |
| Mouse CD14 | L S I A Q A H S L N F S C E Q V R V F P A L S T L D L S D N P E L G E | 205 |

Majority: R G L M A A L C P X K F P A L Q X L A L R N A G M E T P S G V C A A L

| | Sequence | |
|---|---|---|
| Bovine CD14 | T G L M A A L C P N K F P A L Q Y L A L R N A G M E T P S G V C A A L | 243 |
| Human CD14 | R G L M A A L C P H K F P A I Q N L A L R N T G M E T P T G V C A A L | 244 |
| Mouse CD14 | R G L I S A L C P L K F P T L Q V L A L R N A G M E T P S G V C S A L | 240 |

FIG. 7 A

```
Majority      A A A R V Q P Q S L D L S H N S L R X T - A P G A P R C X W P S A L N
                        250                 260                 270                 280
Bovine CD14   A A A R V Q P Q S L D L S H N S L R V T - A P G A T R C V W P S A L R   277
Human  CD14   A A A G V Q P H S L D L S H N S L R A T V N P S A P R C M W S S A L N   279
Mouse  CD14   A A A R V Q L Q G L D L S H N S L R D A - A - G A P S C D W P S Q L N   273

Majority      S L N L S F A G L E Q V P K G L P A K L S V L D L S C N R L X R X P X
                        290                 300                 310
Bovine CD14   S L N L S F A G L E Q V P K G L P P K L S V L D L S C N K L S R E P R   312
Human  CD14   S L N L S F A G L E Q V P K G L P A K L R V L D L S C N R L N R A P Q   314
Mouse  CD14   S L N L S F T G L K Q V P K G L P A K L S V L D L S Y N R L D R N P S   308

Majority      P D E L P E V X N L T L D G N P F L D P G X X X X H X X X M N S G V V
                        320                 330                 340                 350
Bovine CD14   R D E L P E V N D L T L D G N P F L D P G A L Q H Q N D P M I S G V V   347
Human  CD14   P D E L P E V D N L T L D G N P F L V P G T A L P H E G S M N S G V V   349
Mouse  CD14   P D E L P Q V G N L S L K G N P F L D - - - S E S H S E K F N S G V V   340

Majority      P A C A R S X L X V G V S G T L A L L Q G A R G F A
                        360                 370
Bovine CD14   P A C A R S A L T M G V S G A L A L L Q G A R G F A                     373
Human  CD14   P A C A R S T L S V G V S G T L V L L Q G A R G F A                     375
Mouse  CD14   T A G A P S S Q A V A L S G T L A L L L G D R L F V                     366
```

Baculovirus expression system

Forward 5'- GCT AGC GCT AGC CAC CAT GGT GTG CGT GCC CTA CCT GCT - 3'

Reverse 5' - GCT AGC GCT AGC CGC GAA GCC TCG GGC TCC TTG AAG - 3'

B

Mammalian expression system

Forward 5' - CTC GAG CTC GAG GCT AGC CAC CAT GGT GTG CGT GCC - 3'

Reverse 5' - CTC GAGCTGAG GGA TCC CTA AGC GTA ATC TGG AAC - 3'

FIG. 8

Populations: 1 - unfractionated splenocytes
2 - T-depleted, ρ=1.085/1.079 splenocytes
3 - FACS purified mIg$^+$ B cells from population 2

Silver Stain · Immunoblot

Derivation nHu - urine from nephrotic patient
nBo - colostrum
nMo - OKT3-hybridoma supernatant Derivation nBo - colostrum
nHu - urine from nephrotic patients
nMo - OKT3-hybridoma supernatant A. Cord B Cells
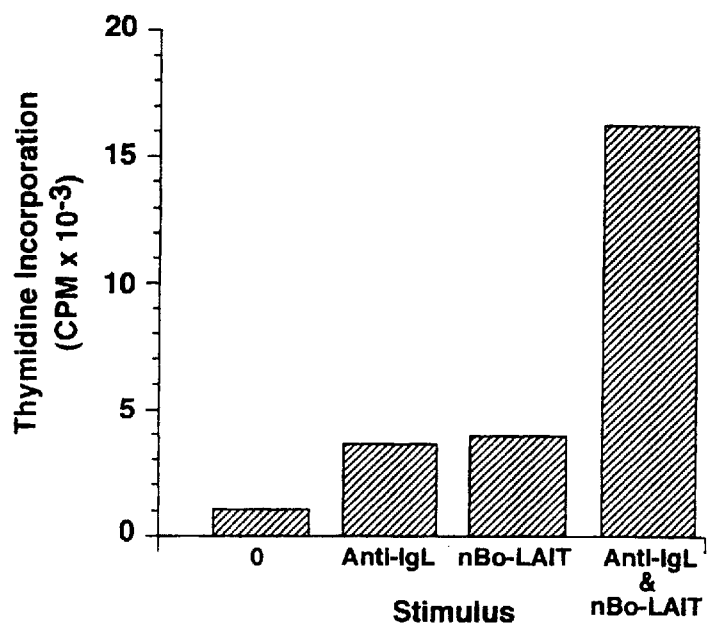
B. Tonsil B Cells
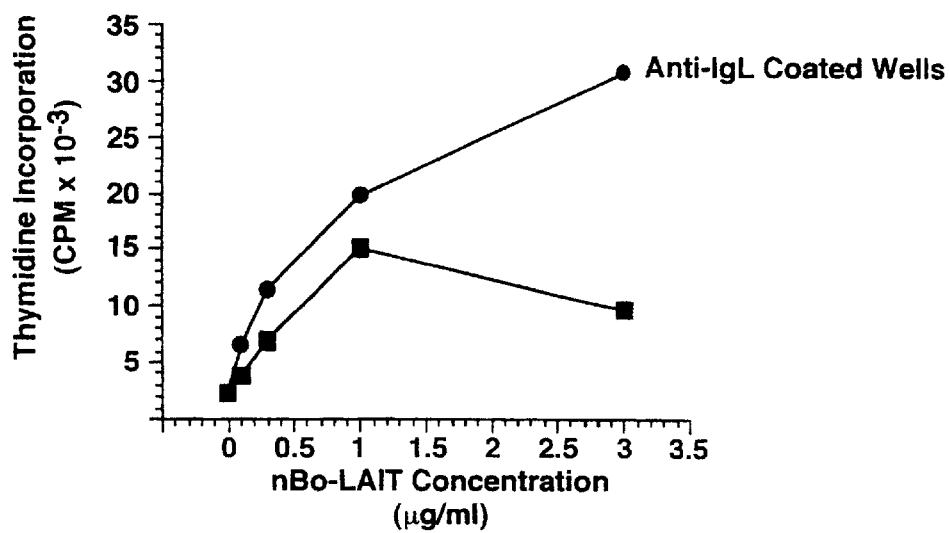
FIG. 20

BOVINE LACTATION ASSOCIATED IMMUNOTROPIC PROTEIN (CD14), ENCODING GENE AND APPLICATION IN B CELL ACTIVATION

This application is a continuation of international patent application No. PCT/CA 97/00880, filed Nov. 18, 1997, which is a continuation-in-part application of U.S. patent application Ser. No. 08/746,883, filed Nov. 18, 1996, now U.S. Pat. No. 6,093,693.

FIELD OF INVENTION

This invention, in the fields of immunology, biochemistry and cell and molecular biology, relates to proteins or proteins that are co- and/or post-translationally modified, termed LAIT proteins, that activate B cells. This invention is also directed to the use of such protein in pharmaceutical preparations, and pharmaceutical compositions comprising LAIT protein or functional derivatives thereof. This invention is also directed to nucleic acid molecules encoding the bovine LAIT protein or functional derivatives thereof and methods for the purification of native and recombinant forms of said proteins that activate B cells.

BACKGROUND OF THE INVENTION

Bone marrow-derived "B" lymphocytes, commonly called B cells, are a type of white blood cell present in the lymph, the blood, and in secondary lymphoid organs of the immune system. B cells are the precursors of antibody secreting cells, plasma cells, and as such are central to the induction of humoral immune responses.

The induction of most humoral immune responses in the adult involves a number of cellular interactions among thymus-derived T lymphocytes, commonly called T cells, antigen presenting cells (APC), and B cells [J. Exp. Med 147:1159, 1978; PNAS 77:1612, 1982; PNAS 79:1989, 1982; Immunol. Rev. 95:914, 1987].

As currently understood, T cell-dependent B cell activation involves activation of T cells upon their recognition of antigen, as presented by APC in conjunction with proteins encoded within the major histocompatibility complex (MHC), which are expressed on the cell surface of the APC. This antigen specific and MHC restricted T cell-APC interaction results in reciprocal activation of the two cell types, and the alteration of T cell physiology such that "helper function" becomes manifest.

Helper T cells can activate antigen specific B cells. Antigen specificity of the T cell-B cell interaction is maintained as a consequence of the ultimate capacity of the B cell to function as an APC. Thus, while resting, quiescent B cells are not efficient APC (PNAS 79: 1989, 1982), they specifically interact with antigen through membrane associated immunoglobulin, the specificity of which reflects that of the immunoglobulin their daughter cells will secrete (J. Exp. Med. 140:904, 1974).

Immunoglobulin mediated internalization of antigen by the specific B cell, which may involve presentation by yet another sort of APC, the follicular dendritic cell, results in the initiation of antigen processing by the B cell, the up-regulation of MHC Class II and B7 expressior., and the presentation of antigen derived peptides in the context of MHC (J. Exp. Med. 178: 2055, 1993). The B cell activated by this route is a target for the activated helper T cell.

T cell helper function includes signals delivered through both T cell-B cell contact, and the interaction of T cell derived soluble mediators, referred to as cytokines, with their cognate ligands expressed on the B cell plasma membrane. T cell-B cell contact is also MHC restricted, analogous to the T cell-APC interaction (Eur. J. Immunol. 12:627, 1982; Eur. J. Immunol. 12:634, 1982). However, the specific interaction of the molecules which mediate the MHC restricted interaction between the two lymphocyte lineages, specifically, the T cell receptor for antigen (TcR), and the MHC/antigen complex expressed by the B cells, do not predicate the induction of B cell growth and differentiation (Eur. J. Immunol. 18:375, 1988).

The essential molecular interaction, reflected by the requirement for T cell-B cell contact, is mediated by CD40 expressed on the plasma membrane of the B cell, and its cognate ligand, gp39 (or CD40L), expressed on the plasma membrane of the T cell (PNAS 89:6550, 1992; Nature 357:80, 1992). Consistent with this paradigm is the observation that membrane expression of the latter increases upon T cell-APC interaction, as well as subsequent to T cell-B cell interaction (PNAS 89:6550, 1992). Further, membrane immunoglobulin mediated B cell interaction with antigen results in the increased membrane expression of CD40 (Sem. in Immunol 6:303, 1994). The interaction between CD40 and CD40L predicates the induction of B cell growth, B cell differentiation into immunoglobulin secreting cells, and immunoglobulin isotype switching (J. Exp. Med. 178:1567, 1993).

Consistent with this model is the observation that soluble CD40L, or monoclonal antibody (mAb) specific for CD40 can induce B cell growth and differentiation to immunoglobulin secretion (Sem. in Immunol. 6:267, 1994; PNAS 83:4494, 1986; J. Immunol. 140:1425, 1988;).

In addition to the obligate requirement for T cell-B cell contact, a number of T cell derived cytokines, IL-2, IL-4 and IL-5 are central to B cell growth and differentiation. B cell susceptibility to these cytokines is for the most part limited by prior contact with a T cell. Thus, subsequent to T cell contact, the B cells increase expression of cytokine specific membrane receptors (PNAS 80:6628, 1983; J. Immunol. 145:2025, 1990; J. Immunol. 146:1118, 1991). IL-2 and IL-5 have been demonstrated to support the growth of activated B cells (PNAS 77:1612, 1980; Immunol. Rev. 52;115, 1980). Further, IL-4 and anti-immunoglobulin have been shown to synergize in supporting B cell growth (J. Exp. Med. 155:914, 1982).

Notable exceptions in this context are the quiescent B cell responses to IL-4 and IL-5. IL-4 induces the de novo transcription and translation of MHC Class II proteins (J. Exp. Med. 155:914, 1982; PNAS 81:6149, 1984; J. Exp. Med. 160;679, 1984), and IL-5 is able to support the differentiation of quiescent B cells into high rate immunoglobulin secreting cells in the absence of cell growth (Eur. J. Immunol. 22:2323, 1992).

In any event, signals derived from molecular interactions amongst membrane molecules on T cells and B cells, and from those of T cell derived cytokines interacting with their cognate receptors on B cells are parts of a complex signaling system. Each signal drives the B cell to another stage of activation, rendering it susceptible to subsequent progression signals. These signals complement one another, rather than having the capacity, individually, to drive the complete process of B cell growth and differentiation (Immunol. Rev. 95:177, 1987).

In 1988, a unique activity in ovine colostrum was discovered (J. Immunol. 140:1366, 1988). Proline Rich Protein (PRP) had been partially purified using classical techniques of protein purification. This material was shown to support the induction of quiescent B cells into the cell cycle, and to support their differentiation into high rate immunoglobulin secreting cells. This was apparently the first report of a protein of mammalian origin that mediates these functions.

A monoclonal antibody specific for ovine PRP was subsequently prepared. When PRP preparations were passed over an affinity column prepared using the antibody, all of the PRP was retained by the column, as assessed by Western blotting analysis of eluate and effluent. However, all of the B cell stimulatory activity was found in the effluent. Thus, the published characterization of the B cell tropic bioactivity present in ovine colostrum was not attributable to PRP (unpublished information).

SUMMARY OF THE INVENTION

This invention features a novel bovine protein and isolated nucleotide sequences encoding the protein, the said protein being capable of activating B-cells of mammalian origin. A substantially pure LAIT protein or co- and/or post-translationally modified form of the protein may be produced by biochemical purification, or by recombinant means in a prokaryotic or eukaryotic host substantially free of other proteins with which it is natively associated. Also included in this invention is a process for purifying LAIT protein or a co- and/or post-translationally modified form of LAIT protein of this invention from bovine colostral whey comprising:

(i) salting out of proteins contained within said samples (ii) enrichment and ultimate purification of LAIT protein from proteins salted out in step (i) utilizing classical protein fractionation techniques.

In all cases the said protein possesses the desired biological activity.

The invention is also directed to a nucleic acid molecule comprising a nucleotide sequence encoding a LAIT protein. The nucleic acid molecule may be cDNA or genomic DNA.

The isolated bovine protein has homology with human CD14 and murine CD14 and so is also referred to as bovine CD14. The invention includes a method of activating B cells, and particularly of activating B cells in a mammal in need of such activation by administering CD14, a recombinant form of the protein thereof, or a functional derivative thereof.

In a preferred embodiment, the mammal is a human patient.

According to one aspect, the invention includes incorporating CD14 into infant formula. The invention includes administering CD14 to an infant, a preferred mode of administration being feeding to the infant such formula.

In another aspect, the invention includes incorporating CD14 as part of a vaccination. The invention includes administering CD14 and antigen to a patient in need of immunization, a preferred mode of administration including administering a single preparation containing both CD14 and the antigen.

In another aspect, the invention includes administering CD14 to a patient having a T cell immune deficiency. In a preferred aspect, the invention includes administering CD14 to a patient suffering from a particular T cell dysfunction in which gp39 (CD40L) is under expressed on or totally absent from the cell surface of patient T cells.

In another aspect, the invention includes administering antibodies raised against CD14 to a patient suffering from a dysfunction wherein the patient's B cells are hyperactivated as a result of higher than normal levels of serum CD14. In a preferred aspect, the invention includes administering antibodies against CD14 to a patient suffering from rheumatoid arthritis wherein the B cells are secreting rheumatoid factor as a result of being activated by serum CD14.

This invention includes a novel method of the production of hybridomas secreting mAb of desired specificity by cuturing B cells with sub-optimal mitogenic concentrations of CD14 in concert with the antigen to which antibodies wished to be raised against. Populations of B cells activated in this manner are highly enriched for activated, antigen specific B cells, which are then be used for the production of hybridomas secreting the mAb of desired specificity.

The invention includes use of CD14 in preparation of medicaments for activating B cells in a mammal in need of such activation.

Natural or recombinant CD14 can be used in the invention.

In the context of this invention, the term "CD14" includes murine, bovine or human CD14.

DEFINITION OF TERMS

A "functional derivative" retains at least a portion of the function of CD14, such as binding to a specific antibody or binding to its cognate receptor on cells that possess said receptor which permits its utility in accordance with the present invention. The term "functional derivative" as used herein includes a "fragment," or "variant" of CD14, which terms are defined below.

A "fragment" of CD14 refers to any subset of the polypeptide, that is, a shorter peptide. The term "fragment" is used to indicate a polypeptide which is derived from CD14 having a naturally occuring protein sequence comprising a deletion of one or more amino acids at one or more sites of the C-terminal, N-terminal, and within the sequence. Such fragments should retain one or more biological activities or functions which are characteristic for the intact CD14 polypeptide or co- and/or post-translationally modified forms of CD14.

A "variant" of CD14 refers to a polypeptide having a primary sequence similar to that of the native CD14 or fragment thereof such that native activity is at least partially retained. Variant peptides may be prepared by synthetic means or by mutations in the cDNA encoding said polypeptide that retains biological activity of said polypeptide including deletions, insertions or conservative amino acid substitutions within the polypeptide.

The term "antibody" as used herein is an immunoglobulin protein that has the capability to bind a distinct epitope in an unconserved region of said protein thereby enabling the antibody to distinguish one protein from another. The term "epitope" is meant to refer to that portion of any molecule capable of being bound by an antibody. The term "antibody" includes polyclonal antibodies, monoclonal antibodies (mAbs) or chimeric antibodies.

Polyclonal antibodies are heterogenous populations of antibody molecules derived from the sera of animals immunized with an antigen.

Monoclonal antibodies are a homogenous population of antibodies capable of binding a distinct epitope on the antigen. MAbs may be obtained by methods known to those skilled in the art. Such antibodies may be of any immunoglobulin class including IgG, IgM, IgE, IgA, and IgD, and any subclass thereof. The term "antibody" is also meant to include both intact molecules as well as fragments thereof, such as, for example Fab and F(ab')$_2$, which are capable of binding antigen. Fab and F(ab')$_2$ lack the Fc fragment of the intact antibody, clear more rapidly from the circulation, and may have less non-specific tissue binding than an intact antibody (Wahl et al., J. Nucl. Med. 24:316–325, 1983).

Chimeric antibodies are molecules, different portions of which are derived from different animal species, such as those having variable region derived from a murine mAb and a constant region derived from a human immunoglobulin.

An "antigen" is a molecule or a portion of a molecule capable of being bound by an antibody which is additionally capable of inducing an animal to produce an antibody capable of binding to an epitope of that antigen. An antigen may have one, or more than one epitope. When an antibody is said to be "specific for" a polypeptide, fragment, or variant thereof or is said to be "capable of binding" to a polypeptide, fragment, or variant thereof it is meant that the antigen will react in a highly selective manner, with its corresponding antibody and not with the multitude of other antibodies which may be evoked by other antigens.

BRIEF DESCRIPTION OF THE DRAWINGS

FIG. 1A shows an elution profile from an anion exchange column [FPLC-Mono-Q(TM), Pharmacia] onto which was loaded 50 mg of the 82% (v/v) $(NH_4)_2SO_4$ precipitate. Bound proteins were eluted with a gradient of 50–400 mM NaCl in 10 mM Bis-tris propane, and a simultaneous pH gradient of 7.5 to 9.6. Table 1A indicates the bioactivity of the fraction with peak activity, fraction #57. High buoyant density mouse spienic B cells were Isolated as previously described (J. Immunol. 131:581, 1983), and cultured at $5 \times 10^4$ cellls in 0.2 ml of serum free medium. In a 96 well cluster, flat bottomed tissue culture plate (Costar). Each fraction was added to a final concentration of 10% (v/v) in the presence, or absence of 0.25 µg/ml LPS. At 40 hours, cultures were pulsed with 1 µCi of $^3$H-TdR, harvested onto filter discs 6 hours later, and thymidine uptake assessed by scintillation spectroscopy. Numbers represent cpm×10$^{-3}$. Panel B shows a profile from a molecular sieving column [FPLC8uperdex 75(TM), Pharmacia] onto which was loaded 20 mg of Fraction #57 (FIG. 1A). The column was equilibriated in 20 mM tris-HCL pH 8.0 buffer containing 0.45M NaCl. Table 1B indicates the bioactivity of the peak fraction, fraction #38, assessed as described in connection with FIG. 1A. Panel C shows the elution profile of a hydroxy apatite column [HPLC-hydroxy apatite, Pharmacia] onto which was loaded 1 mg of fraction #38 (Panel B). Bound proteins were eluted with a a gradient of 1–500 mM $K_2HPO_4$ buffer, pH 6.8 containing 1 mM NaCl. Table 1C indicates the bioactivity of the peak fraction, fraction #25, assessed as described in connection with Panel A, The inset in the figure shows a silver stained SDS-PAGE gel of roughly 5 µg of protein from fraction #25. Left lane: fraction #25; right lane, MW markers, from the top: 97, 66, 45, 31, 21, and 14 kD, respectively.

FIG. 2 shows the known sequence of human CD14 (SEQ ID NO:5) and aligned fragments of nBo-LAIT. Bo-LAIT fragments were generated from affinity purified colostral nBo-LAIT (see FIG. 3). Fragments corresponding to residues 235–264 and 344–355 of human CD14 were major and minor peptides, respectively, each approximately 18 kD in size, generated by CnBr cleavage, and separated by reverse phase HPLC (C8 column, Pharmacia). The fragment corresponding to residues 53–67 of human CD14 is a partial sequence of a 24 kD fragment generated by CnBr cleavage, and separated by SDS-PAGE and electroblotted onto PVDF membrane. Fragments corresponding to residues 19–36 and 151–165 of human CD14 were generated by trypsin cleavage, and separated by reverse phase HPLC (C8 column, Pharmacia). The length of the overlapping bovine sequence with the predicted sequence of human CD14 is underlined for each of the fragments. Dashes indicate the same amino acids while those differing from the human sequence are indicated.

FIG. 5(Panel B) is a schematic diagram of the bovine CD14 locus. The shaded area represents the coding region of the gene, the open box is an intron sequence. The dashed area in front of the ATG start codori is 5' untranslated region, and the dashed area behind the TAA stop codon is 3' untranslated region. FIG. 5 (Panel C) is a schematic diagram showing the sequencing strategy taken. Arrows represent the direction of sequencing. The fragment number is indicated at the right (see text for detail).

FIGS. 6A–6E shows a comparison of nucleic acid sequences of bovine (SEQ ID NO:1), human (SEQ ID NO:2) and mouse (SEQ ID NO:3) CD14 coding regions. The first base position corresponds to the first nucleotide of the ATG codon, the last nucleotide corresponds to the third nucleotide of the TAA stop codon. Alignment was done using DNA STAR-Megalign software, applying the Clustal method with a weighted residue table. Human cDNA sequence (accession number P08571) and mouse cDNA sequence (accession number P08571) used in this alignment were derived from the Swiss-Protein Database.

FIGS. 7A–7B shows a comparison of amino acid sequences of bovine (SEQ ID NO:4), human (SEQ ID NO:5) and mouse (SEQ ID NO:6) CD14 proteins. Amino acid sequences were deduced from the corresponding cDNA sequences shown in FIG. 6. DNA Star-Megalign software was used to generate this alignment using the method described by J. Hein (Methods in Enzymology 183:626, 1990) in conjunction with the PAM 250 residue weight table.

FIG. 8 (Panel A–B) show primers used for amplification of Bovine CD14 cDNA coding region. Panel A shows forward (SEQ ID NO:7) and reverse (SEQ ID NO:8) primers used for the baculovirus expression system. Panel B shows forward (SEQ ID NO: 9) and reverse (SEQ ID NO: 10) primers used for the mammalian expression system.

Figure 15:
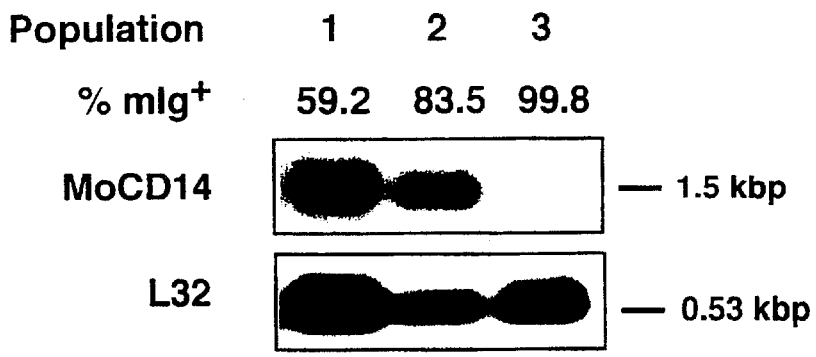
FIG. 15 shows a Northern Blot analysis for CD14 contained in: (1) unfractionated splenocytes, (2) high buoyant density, resting, murine splenic B cells prepared as described for FIG. 1A, and (3) FACS sorted $mIg^+$ B cells derived from the latter high buoyant density resting population. For FACS sorting, high buoyant density cells were incubated with FITC-conjugated mAb 187.1, specific for mouse Igκ (Hybridoma 1:5, 1981). The proportion of $mIg^+$ cells in each of the three populations is indicated. Total RNA was isolated from $10^7$ cells of each of the three populations using the Trizol method (Gibco BRL Life Technologies) according to the manufacture's instructions and resolved on a 1.2% formaldehyde gel. RNA was transferred to a nylon membrane (GeneScreen) using the vacuum blotting system (Pharmacia). Cross linking, prehybridization and hybridization were performed as recommended by the membrane manufacturer. The murine CD14 specific probe was derived from a genomic mouse CD14 fragment generated by PCR using the forward primer 5'-CTA GAA TTC TCT CCC GCC CCA CCA GAG CCC TGC G-3' (SEQ ID NO:11), and reverse primer 5'-CTA GAA TTC TTA AAC AAA GAG GCG ATC TCC TAG G-3'(SEQ ID NO:12). The amplified fragment was resolved by agarose gel electrophoresis, excised and purified. An L-32 cDNA probe (Nucl. Acid Res. 16:10751, 1988), specific for a constitutively expressed mRNA of the large ribosomal subunit protein was used to normalize RNA loading. The probes (100 ng each) were labeled using oligolabeling kit (Pharmacia) to a specific activity of $0.2-1\times10^9$ cpm/μg of DNA. The membrane was then washed in 0.2×SSC, 1% SDS at 65° C. for 2 hours and exposed to the X-ray film (Kodak, Biomax MS) for 1 to 5 days.
Figure 16:
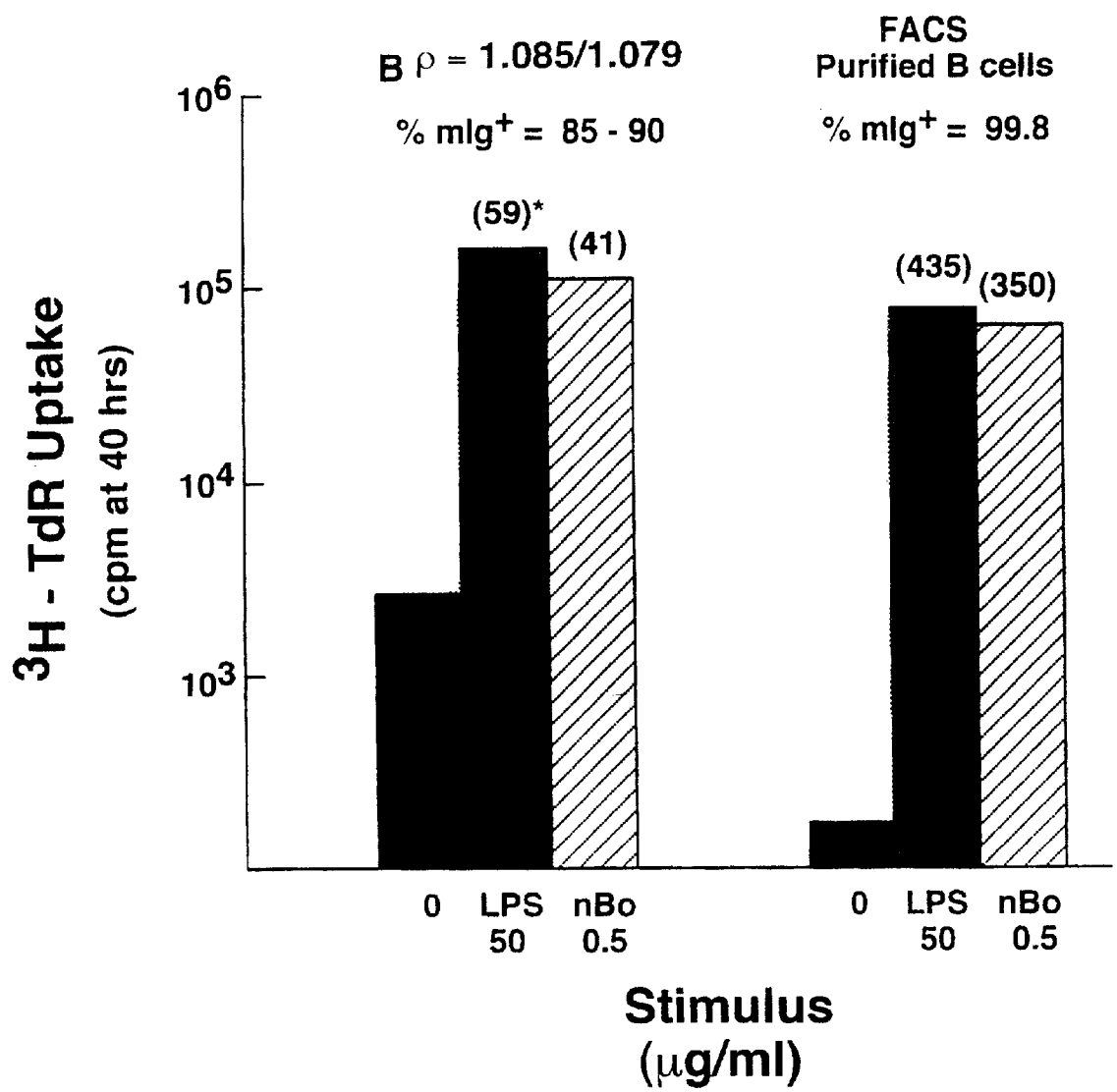

FIG. 16 shows the response of high buoyant density, resting, murine splenic B cells that were further purified for mIg$^+$ cells as described in FIG. 15, or not, to 50 μg/ml LPS [S.typhosa (Difco)] and 0.5 μg/ml of affinity purified nBo-LAIT. Cultures were established, pulsed with tritiated thymidine, harvested, and thymidine uptake assessed as described for FIG. 1A. Numbers indicated represent the average cpm of duplicate cultures.

Figure 17:
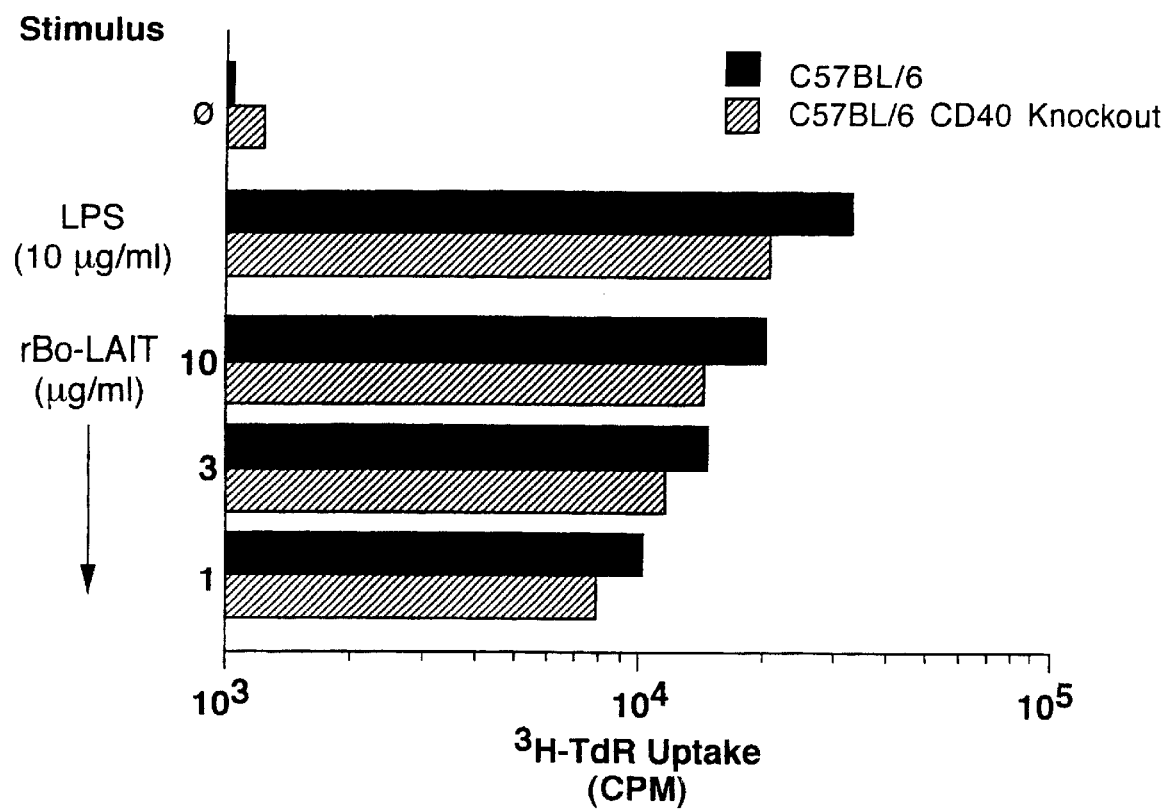

FIG. 17 shows the CD40 independence of recombinant Bo-LAIT mediated B cell activation. High buoyant density, resting, murine splenic B cells were isolated from either conventional C57BL/6 mice, or from CD40 deficient animals created by targeted disruption of the CD40 locus (Immunity 1:167, 1994). Cells ($1.5\times10^5$) were cultured in the presence of 10 μg/ml LPS, or the indicated concentrations of rBo-LAIT derived in the insect cell expression system. Cultures were pulsed and harvested as described in connection with FIG. 1A. Numbers indicated represent the average cpm of duplicate cultures.

Figure 18:
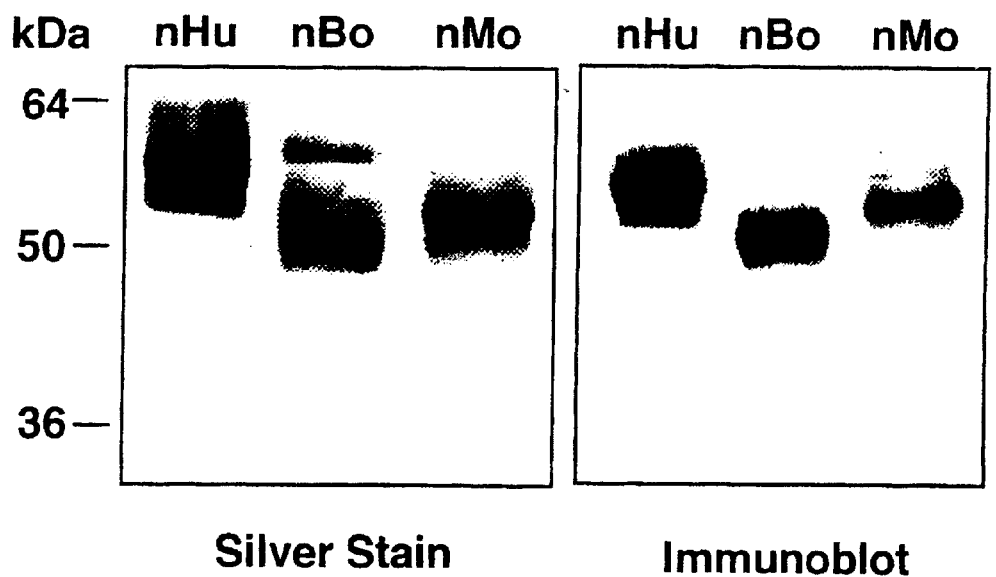

FIG. 18 shows a comparative silver stain (left panel) and immunoblot (right panel) analysis of native CD14 derived from human (nHu), cow (nBo), and mouse (nMo). nHu was isolated from the urine of nephrotic patients, as previously described (Eur. J. Immunol. 24:1779, 1994). nBo was affinity purified from bovine colostrum as described in FIG. 3. nMo was isolated from supernatant of the mouse hybridoma OKT3 (PNAS USA 77:4914, 1980) by affinity chromatography using Sepharose(TM) 48 immobilized CD14 specific mAb 3C10 (J. Exp. Med. 15:126, 1983). For silver staining, 1 μg of each of the samples was resolved on 10% SDS-PAGE at 200V for 45 minutes. Protein was visualized by silver staining (Biorad) following manufacturers Instructions, For immunoblotting, 250 ng of each of the samples was resolved by 10% SDS-PAGE at 180 mA for 45 minutes, electrophoretically transferred to PVDF membrane (Millipore) at 180 mA for 30 minutes. The membrane was blocked for 1 hour in 5% skim milk in TEST (20 mM Tris.HCl, pH 7.5, 150 mM NaCl, 0.025% Tween 20), followed by incubation for 1 hour with mAb 3C10 (J. Exp. Med. 15:126, 1983) at concentration 10 μg/ml in TBST supplemented with 5% skim milk. The blot was rinsed three times for 10 minutes/rinse in TBST. Goat anti-mouse IgG conjugated with horse radish peroxidase (BioRad) was used to detect mouse antibody. The membrane was then rinsed three times (10 minutes/rinse) with TBST. The ECL kit (Amersham) was used to visualize the proteins.

Figure 19:
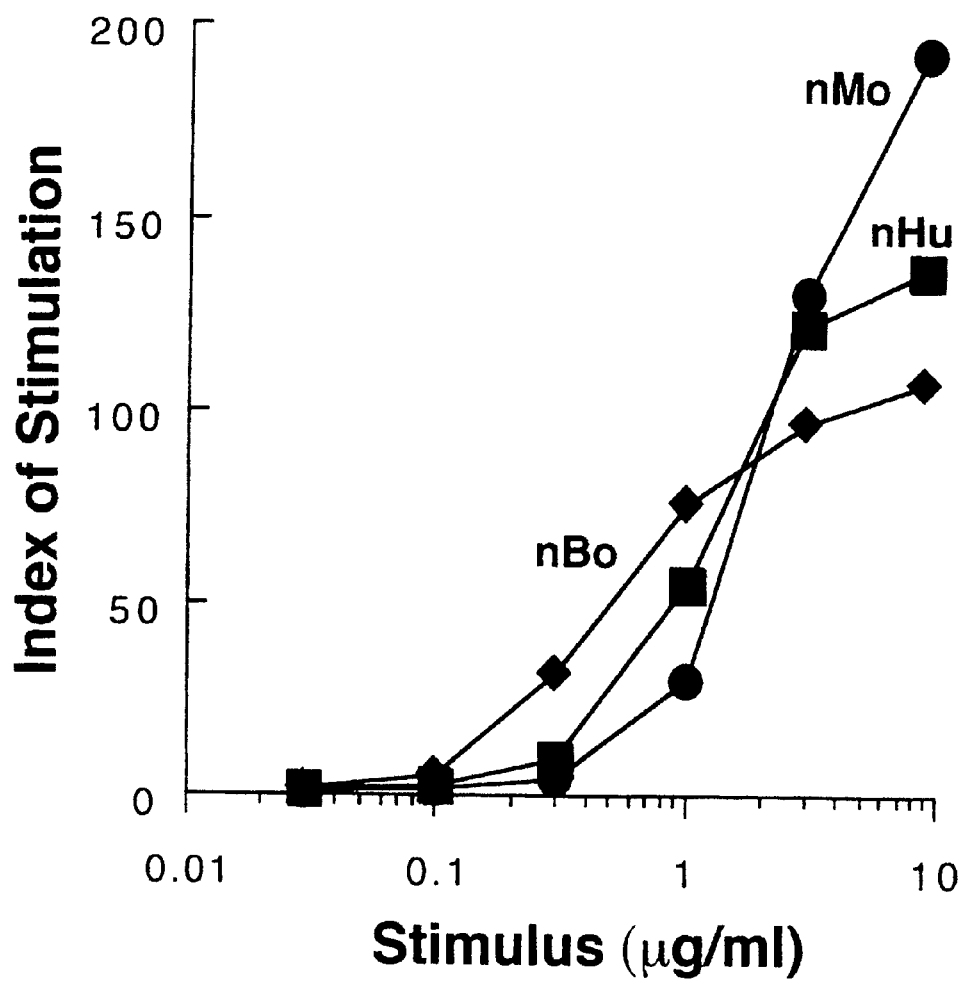

FIG. 19 shows a comparative analysis of native CD14 derived from human (nHu), cow (nBo), and mouse (nMo) to stimulate the growth of murine B cells. These three proteins were purified as described in FIG. 18. The response of high buoyant density, resting, murine splenic B cells isolated as described in FIG. 1A, to the indicated concentrations of the three proteins, was assessed. Cultures were pulsed with 1 μCi of $^3$H-Tdr at 40 hrs and harvested at 46 hrs. The numbers indicated represent the index of stimulation derived by dividing mean cpm of duplicate cultures stimulated with the indicated concentration of nHu, nBo, and nMo, by mean cpm of duplicate cultures containing no stimulus.

FIGS. 20(Panel A–B) shows growth promoting activity of nBo-LAIT on human B cells isolated from cord blood and tonsils, respectively. Panel A shows thymidine uptake by cord blood B cells isolated by positive selection. Cord blood leukocyte suspensions were stained with fluorescein labeled mAb specific for the pan B cell marker CD72. CD72 positive cord leukocytes were then isolated on a fluorescence activated cell sorter (FACStar Plus, Becton Dickenson) resulting in purities of >98%. B cells ($1.5\times10^5$) were cultured as described for FIG. 17(Panel A), in the presence of no stimulus or 2 μg/ml of nBo-LAIT. B cells were also cultured in wells which had been pre-coated for 9 hours with a combination of two mAbs, one specific for human IgK [LO-HK3, (In "Rat Hybridomas and Rat Monoclonal Antibodies" ed. H. Bazin, CRC Press, Boca Raton, Fla., USA)] and one specific for human Igλ [LO-HL-2, (in "Rat Hybridomas and Rat Monoclonal Antibodies" ed. H. Bazin, CRC Press, Boca Raton, Fla., USA)], each at a coating concentration of 1.5 μg/ml, without additional stimulus, or in the presence of 2 μg/ml of nBo-LAIT. Cultures were pulsed at 60 hours with 1 μCi of $^3$H-TdR, harvested onto filter discs 12 hours later, and thymidine uptake assessed by scintillation spectroscopy. Panel B shows results obtained using tonsil B cells prepared by negative selection. Specifically, leukocyte suspensions were labeled with biotinylated mAb specific for CD3ε (Becton Dickenson), followed by avidin conjugated with iron containing "micro-beads" (Becton Dickenson). The labeled population was passed through the MACS (Becton Dickenson), and the effluent collected. This population contained <1% T cells, and >97% B cells as assessed by immunofluorescence staining with lineage specific mAbs. B cells ($1.5\times10^5$) were cultured as described in connection with Panel A, As for cord blood B cells, tonsil B cells were cultured in the presence and absence of plate bound mAbs specific for human Igκ and λ, but in this case, wells were pre-coated using a concentration of 0.5 μg/ml of each of the mAbs. Cultures were pulsed, harvested, and thymidine uptake assessed as described for Panel A.

Figure 21:
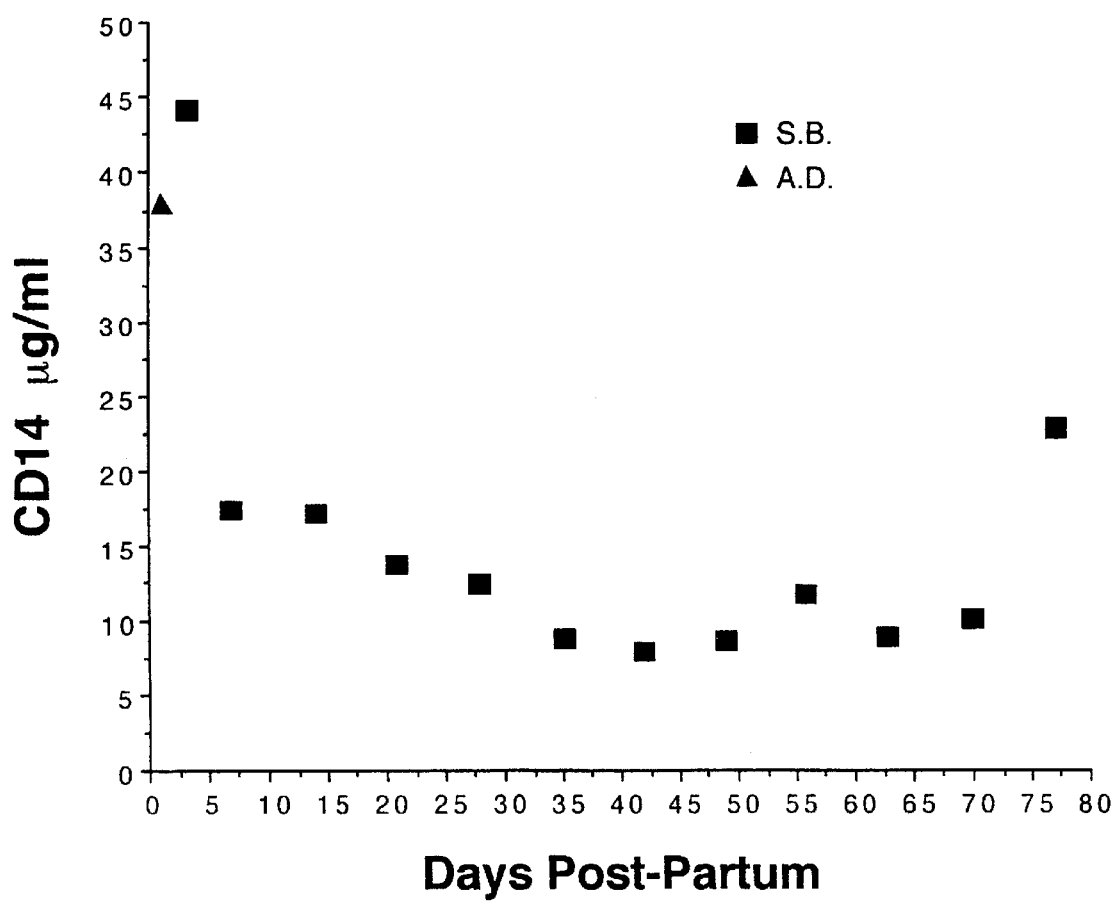

FIG. 21 shows the concentration of CD14 in breast milk over time post-partum. Breast milk was collected from two donors (A.D. and S.B.) at the indicated times postpartum. Clarified whey was prepared, and the concentration of contained CD14 assessed using a CD14 specific ELISA kit (IBL, Hamburg) according to manufacturers instructions.

DESCRIPTION OF PREFERRED EMBODIMENTS

The experiments described below demonstrate purification of native bovine LAIT protein (nBo-LAIT), also referred to herein as bovine CD14, from colostral whey. Amino acid sequence analysis of purified nBo-LAIT is shown, and homology with human CD14 is demonstrated. A method for the purification of human CD14 from is shown. A method for the purification of mouse CD14 from hybridoma supernatant is shown.

In vitro B cell stimulation assays are described for affinity purified colostral Bo-LAIT, human colostral CD14, human CD14 derived from urine, and mouse CD14 derived from a hybridoma supernatant. High buoyant density resting splenic B cells derived from mouse are shown to enter and progress through cell cycle, in response to LAIT protein from the three species, and to differentiate into high rate immunoglobulin secreting cells in response to exposure to LAIT-protein from bovine. These activation events occur in defined serum free medium, and it is also shown that the presence of fetal calf serum in culture medium does not affect LAIT protein mediated B cell activation. Experiments are shown demonstrating that nBo-LAIT specifically activates murine B cells, and not murine T cells, and that LAIT protein activates B cell populations in which CD14 mRNA is undetectable. Experiments demonstrating that bovine CD14 induces growth of B cells in which CD40 is not expressed are also given.

The isolation, cloning and sequencing of both genomic DNA and cDNA encoding bovine CD14 is described. Sequence comparisons with mouse and human CD14s, known in the literature, show the sequence relationship between Bo-LAIT and these previously known CD14s. B cell growth and differentiation activities associated with recombinant bovine CD14 are shown.

Methods for the expression of recombinant bovine CD14 in both insect and mammalian systems are described. Specifically, a baculovirus expression vector was employed in aid of expressing recombinant proteins in insect cells. Comparison of the B cell growth and differentiation properties of native Bo-LAIT (nBo-LAIT) and recombinant Bo-CD14 (rBo-LAIT) derived from the baculovirus expression system revealed that the latter was functional, and had a specific activity of roughly 50% of that of nBo-LAIT.

The mouse mammary carcinoma cell line, C127, was used as a recipient of cDNA encoding CD14 derived from bovine. cDNA was cloned into a bovine papilloma virus expression vector. Stable C127 transfectants were established, and recombinant CD14 protein was isolated from supernatants of confluent C127 cultures by affinity chromatography. Western blot analyses of insect cell and C127 derived recombinant LAIT-proteins revealed that different co- and/or post-translational modifications were generated in the two expression systems. The specific activity of mammalian cell derived recombinant bovine CD14 was the same as that recombinant material derived from insect cells.

A comparison of the B cell growth promoting activity supported by native Bo-LAIT and recombinant bovine CD14 derived from insect cells and mammalian cells is given. Further, growth promoting activity of native Bo-LAIT activities on human B cells, isolated from either tonsils, or from cord blood, is given. Results demonstrate that as for murine B cells, human B cells, isolated from either from a neonate or an adult, are susceptible to Bo-LAIT mediated growth.

It is shown that the concentration of CD14 present in human colostrum, and in breast milk up to 78 days postpartum, is between 3–20-fold higher than that observed in sera from healthy donors.

METHODS

Purification of Bovine LAIT-protein

More than five liters of colostrum was obtained from the first mammary secretions of cows having just given birth.

(i) Clarified colostral whey was prepared by centrifugation of colostrum first at 4420 g for 30 minutes to remove cells and cellular debris. The supernatant of this spin was then centrifuged at 250,000 g for two hours. The floating lipids and the pelleted casein were discarded, and the clarified colostral whey was subjected to further fractionation.

Each fraction derived from each fractionation technique was assessed for B cell growth promoting activity in vitro. Thus, each fraction was assayed over a wide concentration range for its capacity to stimulate the growth of high buoyant density, resting B cells derived from mouse spleen, as previously described (J. Immunol. 131:581, 1983). Defined serum free medium was used throughout these analyses [IMDM (Gibco), supplemented with $5 \times 10^{-5}$ 2-β-mercaptoethanol, 5 µg/ml iron-saturated transferrin (Boehringer, Lewes, GB), 0.5 mg/ml delipidated BSA (Boehringer), 100 U/ml penicillin (Gibco), 100 µg/ml streptomycin (Gibco), and essential amino acids]. Fractions derived from the isolation scheme described below were tested directly, as well as in combination with a submitogenic concentration of LPS (0.25 µg/ml). As will be described, as LAIT protein approached purity, its direct mitogenic properties were revealed.

(ii) Salting out of proteins contained within colostral whey preparations was accomplished using sequential precipitation in $(NH_4)_2SO_4$. The sequence of increasing salt concentrations employed was 42%: 50%: 62%: 65% (v/v) ammonium sulphate (AS). Thus, the concentration of AS in the supernatant of the material precipitated at 42% was increased to 50%; the material precipitated at 50% rescued, and the concentration of AS in the remaining supernatant increased to 62%, and so on. Each AS precipitated pellet was solubilized in 10 mM Tris-HCL pH 8.0, containing 0.15M NaCl and 1 mM AEBSF (TNAEBSF). These fractions were desalted and buffer exchanged to TNAEBSF using 10DG columns, and assayed for bioactivity. The majority of B cell growth promoting activity was isolated in the 62% AS precipitate following the above scheme (not shown).

Figure 1:
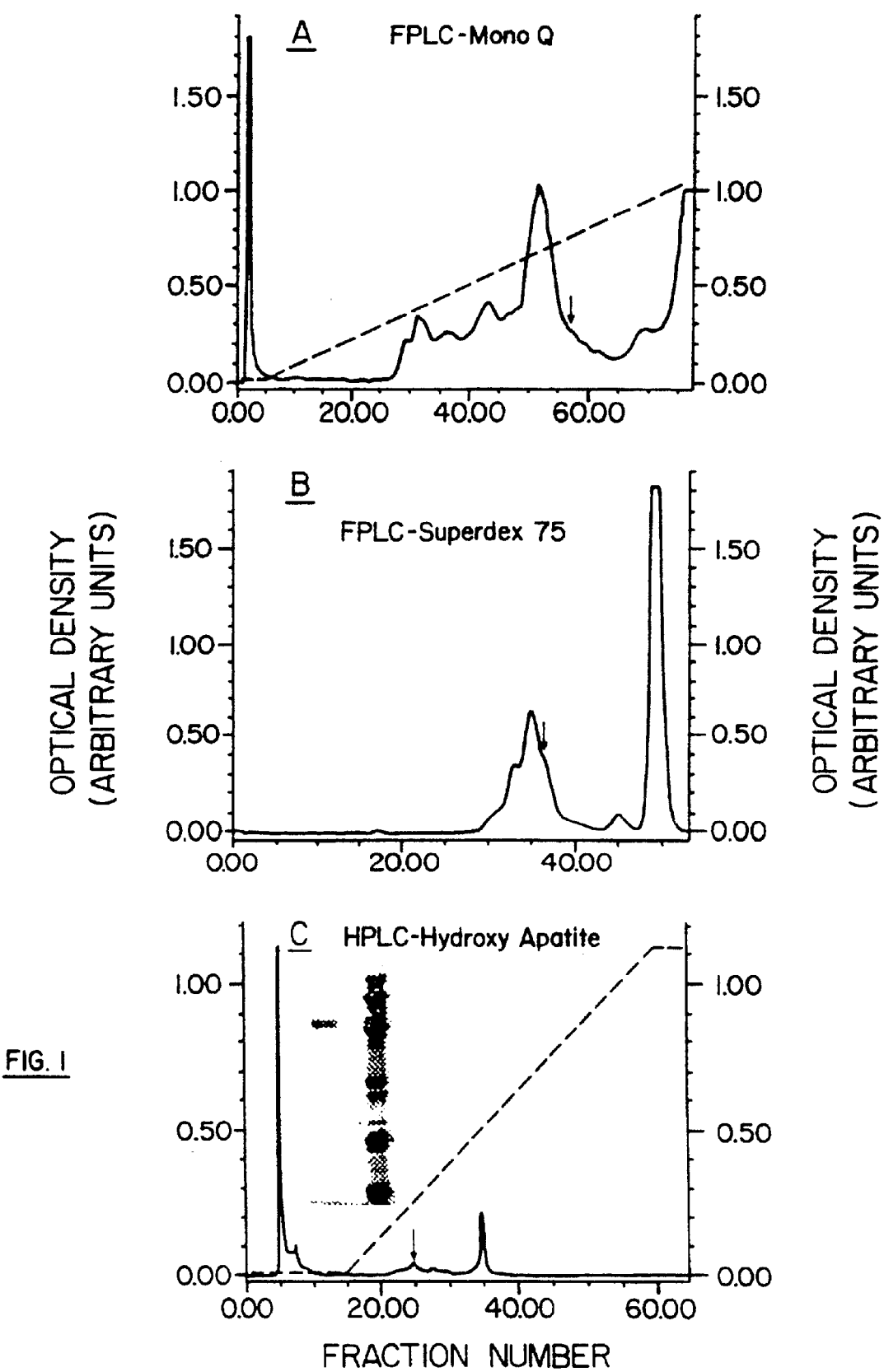
FIG. 1(Panel A–C) show purification of native bovine LAIT (nBo-LAIT) protein.

(iii) Activity was subsequently enriched, and ultimately purified using three sequential protein fractionation techniques. Fifty milligrams of the 62% AS enriched fraction was applied to an anion exchange column, and the material separated using a salt gradient of 50 mM to 400 mM NaCl in 10 mM Bis-tris propane, with a simultaneous pH gradient of 7.5 to 9.5. FIG. 1A shows the elution profile from this column, and Table 1A indicates the fraction containing the peak activity, fraction #57. Twenty milligrams of fraction #57, was then applied to a molecular sieving column equilibrated in 20 mM Tris-HCL, pH 8.0 containing 0.45M NaCl. The elution profile of this fractionation is shown in FIG. 1B and the activity of the peak fraction #38 shown in Table 1B.

TABLE 1A

|  | CPM × 10⁻³ |
| --- | --- |
| NO STIMULUS | 0.8 |
| LPS 50 µg/ml | 152.5 |
| LPS 0.25 µg/ml | 3.9 |
| FRACTION 57 + 0.25 µg/ml LPS | 108.7 |

TABLE 1B

|  | CPM × 10⁻³ |
| --- | --- |
| NO STIMULUS | 0.4 |
| LPS 50 µg/ml | 102.1 |
| LPS 0.25 µg/ml | 1.3 |
| FRACTION 36 + 0.25 µg/ml LPS | 76.0 |

TABLE 1C

| | CPM × 10⁻³ |
|---|---|
| NO STIMULUS | 0.7 |
| LPS 50 μg/ml | 135.2 |
| LPS 0.25 μg/ml | 3.5 |
| FRACTION 25 + 0.25 μg/ml LPS | 112.0 |

One milligram of fraction #38 was then applied to an hydroxy apatite column in 1 mM NaCl, and eluted using a gradient of 1 to 500 mM potassium phosphate buffer pH 6.8. The elution profile is shown in FIG. 1C with the associated activity shown in Table 1C.

The inset in FIG. 1C represents an SDS-PAGE analysis of the fraction with peak activity followed by silver staining, and illustrates a single major band with a relative molecular mass of 46–50 kD.

Sequence Analysis of Bovine LAIT-protein

The purified nBo-LAIT was subjected to sequence analysis. The N-terminus was found to be blocked. The material was subjected to hydrolysis with either cyanogen bromide, or trypsin. Five fragments were generated and these were purified using either reverse phase HPLC, or SDS-PAGE followed by electroblotting onto a PVDF membrane, prior to sequencing.

As illustrated in FIG. 2, the five fragments all aligned, with significant hornology, to human CD14.

Affinity Purification of LAIT Protein From Bovine and Human Colostrum nBo-LAIT isolated using classical protein fractionation techniques was used to prepare a rabbit (#842) polyclonal antibody. The IgG fraction of this antiserum was purified on Protein A-Sepharose(TM), and subsequently conjugated to Sepharose(TM) 4B.

The sequence homology of nBo-LAIT and human CD14 (HuCD14) indicated that Bo-LAIT might be the bovine homologue of CD14. This was further explored by generating an affinity column using available monoclonal antibody (mAb) specific for HuCD14. This antibody, 63D3 (PNAS 77:6764, 1980), was purified from the corresponding hybridoma supematant on an affinity column comprised of mAb 187.1 [rat anti-mouse kappa (Hybridoma 1:5, 1981)], conjugated to Sepharose(TM) 4B, and the purified mAb then conjugated to Sepharose(TM) 4B.

Bovine clarified colostral whey was sequentially salted out using ammonium sulphate, as described above. Human colostral whey was fractionated on a Sephacryl S100 HR column. The fractions containing peak B cell growth promoting activity were then affinity purified using either the 842-Sepharose(TM) column for the bovine material, or the 63D3-Sepharose(TM) column for the human material.

Figure 3:
FIG. 3 shows SDS-PAGE and silver staining of affinity purified colostral LAIT-protein from bovine and human. Lane 1; MW markers, as given for FIG. 1C; lane 2: 62.5% (v/v) $(NH_4)_2SO_4$ precipitate of bovine colostral whey; lane 3; pH 2.5 eluate from #842-Sepharose(TM) affinity column; lane 4; pH 2.5 eluate from CD14 specific mAb 63D3 (PNAS 77:6764, 1980)-Sepharose(TM) affinity column, loaded with material represented in lane 5; lane 5; Sephacryl S100 HR fractionated human colostral whey. Each of lanes 1–5 contain 5 µg of protein. Table 2 shows results obtained when $5 \times 10^4$ high buoyant density mouse splenic B cells were cultured in serum free medium in the presence of the indicated stimuli for 40 hours, pulsed with 1 µCi of $^3$H-TdR, harvested 6 hours later onto filter discs, and thymidine uptake assessed by liquid scintillation spectroscopy. Numbers represent cpm×10$^{-3}$. Details of the bioassay are as described for FIG. 1A. Control cpm×10$^{-3}$: no stimulus, 0.3; 50 µg/ml LPS, 75.0; 025 µg/ml LPS [LPS ↓], 0.8; and 1 µg/ml mIgM specific mAb b-7-6 (Eur. J. Immunol. 14:753, 1984), 0.7.

The SDS-PAGE analysis of affinity purified colostral Bo-LAIT, and affinity purified human colostral CD14 is shown in FIG. 3 and the associated B cell growth promoting activity is shown in Table 2. As illustrated, a predominant band was isolated from both colostral preparations, the p46–50 bovine material (FIG. 3, lane 3) and a p50–52 human molecule (FIG. 3, lane 4).

TABLE 2

| | BOVINE #842 pH 2.5 ELUATE | HUMAN 6303 pH 2.5 ELUATE |
|---|---|---|
| 100 ng/ml | 20.00* | 0.3 |
| 10 ng/ml | 1.49 | 0.3 |
| ● + LPS↓ | 16.5 | 21.1 |
| ● + b-7-6 | 5.17 | 8.5 |

*Numbers represent cpm × 10⁻³ at 40 hours of culture.

The bioactivity shown in Table 2 demonstrates that affinity purified Bo-LAIT, at a concentration of 100 ng/ml, stimulated the growth of resting mouse B cells. When added at 10 ng/ml, this material was no longer mitogenic, but costimulation was achieved upon the addition of either a submitogenic concentration of LPS, or a mAb specific for mouse IgM, b-7-6 (Eur. J. Immunol. 14:753, 19841. The affinity purified human material was not by itself found to be mitogenic at concentrations tested, but at 10 ng/ml, B cell growth was stimulated with the same costimuli as efficiently as with the bovine material.

Figure 4A:
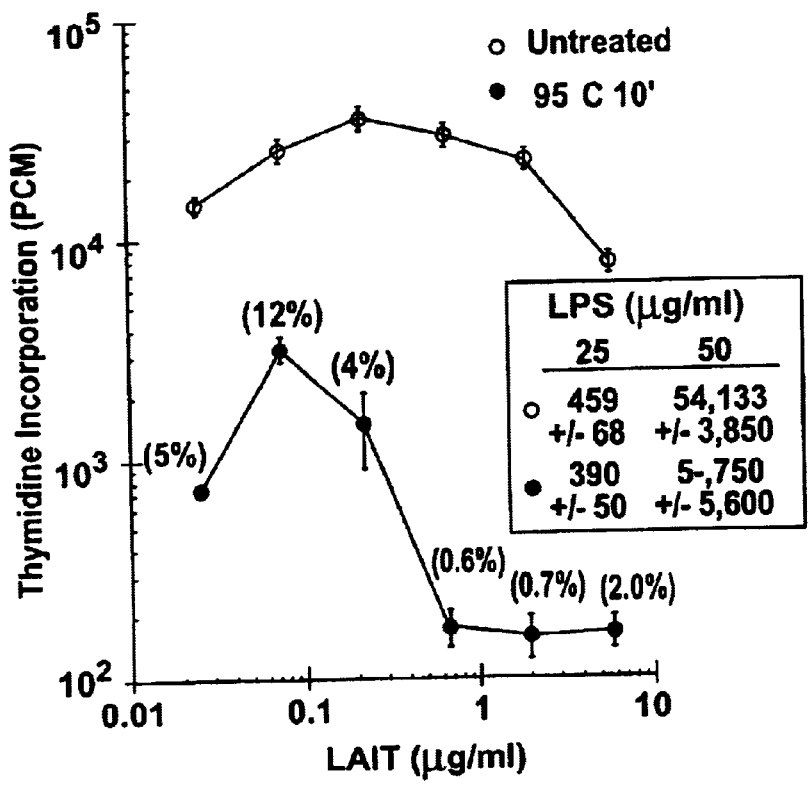
FIG. 4(Panel A–B) show heat lability and antibody mediated inhibition of nBo-LAIT activity. Panel A shows thymidine uptake by $5 \times 10^4$ high buoyant density mouse splenic B cells cultured as described for Panel A in the presence of the indicated concentration of affinity purified nBo-LAIT that had been heat treated at 95° C. for 10 minutes (●), and nBo-LAIT that had not been heat treated (○). Cultures were pulsed with $^3$H-TdR at 40 hours, harvested 6 hours later, and thymidine uptake assessed by liquid scintillation spectroscopy. The inset depicts the responses in cultures containing the indicated concentrations of LPS, which had been heat treated (or not) as for nBo-LAIT. Panel B shows thymidine uptake in cultures that were established as described for Panel A in the presence of either 0.25 µg/ml of affinity purified nBo-LAIT, or 50 µg/ml of LPS. Each of these stimuli were cultured in the presence of the indicated concentration of either polyclonal rabbit IgG anti-Bo-LAIT, #842, or normal rabbit IgG. The percent inhibition of thymidine uptake mediated by #842 IgG for both nBo-LAIT and LPS mediated stimulation is indicated in parentheses. Levels of inhibition mediated by normal rabbit IgG ranged from 9–20%, and 12–31% for nBo-LAIT and LPS stimulation, respectively. CPM directly induced by #842 IgG in isolation ranged from 454±53 to 764±69 at 0.4 and 50 µg/ml, respectively; and for normal rabbit IgG, from 297±34 to 420±31 at 0.4 and 50 µg/ml, respectively. Non-stimulated controls gave rise to 195±29 cpm for both sets of experiments.
Figure 4B:
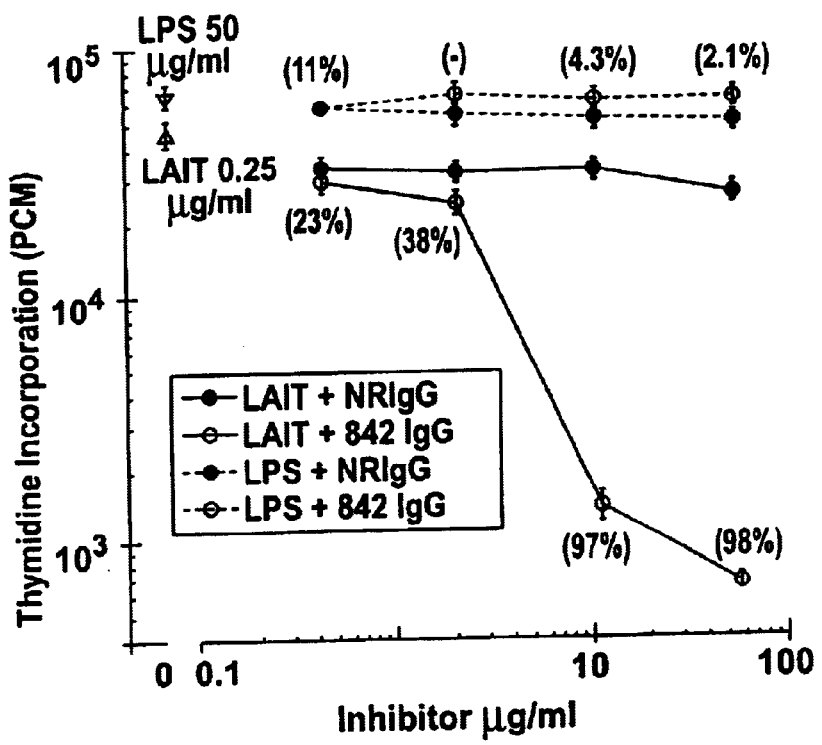

The bioactivity of nBo-LAIT is heat labile. As illustrated in FIG. 4A, treatment of affinity purified Bo-LAIT at 95° C. for 10 minutes abolishes the associated B cell growth promoting activity. Similar treatment of LPS had no effect on its activity (inset of FIG. 4A). Further, the polyclonal anti-Bo-LAIT, #842, efficiently blocked the B cell growth promoting activity of nBo-LAIT, while not affecting the activity of LPS. See FIG. 4B and inset.

Molecular Cloning of Genomic Bovine CD14

A bovine genomic EMBL-3 SP6/T7 lambda library (Clontech) was screened with a 1.5 kb fragment of human CD14 cDNA (obtained from R.Ulevitch, Scripps Institute). Fifteen positive signals were obtained, and the strongest signal, clone "B2" was chosen for further analysis and cloning of bovine CD14.

Figure 5:
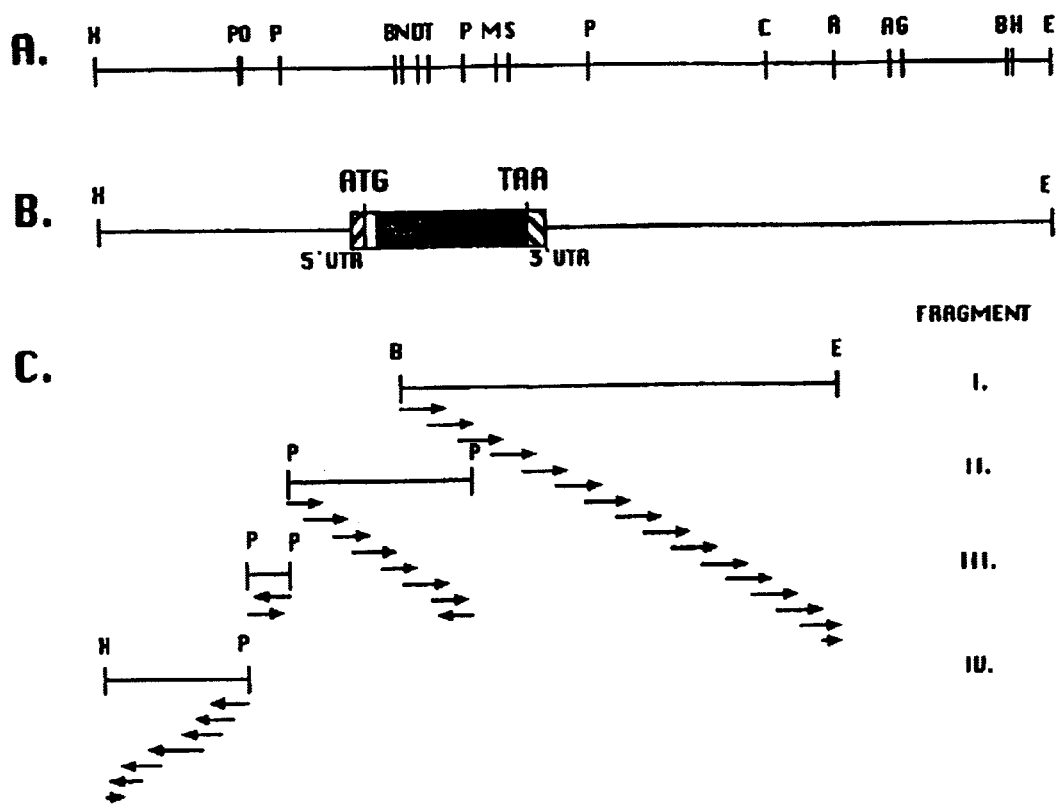
FIG. 5(Panel A) shows a restriction map of the 7.1 kb EcoRI-XhoI fragment containing bovine CD14 gene. Abbreviation for restriction sites are: X. XhoI; P, PstI; O, NcoI; B, BamHI; N, NotI; D, BssHI; T., BstEII; M, SmaI; S, SacII; C, HpaI; R, EcoRV; A, SphI; G, BglIII; H, HindIII; E, EcoRI.

Isolated and purified phage DNA from clone B2 had an insert size of roughly 15 kb. Purified DNA was digested, and a resulting 7.1 kb EcoRI-XhoI fragment, containing a homologous sequence to human CD14, was subcloned into pBluescriptSK⁺ (Stratagene). Restriction mapping, utilizing a wide range of enzymes, followed by hybridization with the human CD14 probe enabled the localization of the bovine CD14 gene within the cloned fragment (FIG. 5A). Further restriction mapping was used for the subcloning of four shorter fragments (I–IV) into pBluescriptSK⁺, and the subsequent sequencing of roughly 5 kb encompassing the entire bovine CD14 gene (FIG. 5C). Fragment I (EcoRI-BamHI, 3.2 kb); II (PstI-PstI, 1.35 kb); III (PstI-PstI, 0.3 kb); and IV (PstI-XhoI, 0.95 kb), were used to construct nested overlapping unidirectional deletions. These fragments provided contiguous sequence of the bovine CD14 locus. FIG. 5B depicts the organization of the bovine CD14 genomic fragment.

Molecular Cloning of Bovine CD14 cDNA

Poly(A⁺) RNA was isolated from bovine peripheral blood monocytes, and Gigapack II Packaging Extract (Stratagene) was used to package recombinant lambda phage DNAs. A cDNA library was prepared using the ExceII EcoRI/CIP vector with the "Time Saver cDNA Synthesis Kit" (Pharmacia).

The library was screened with the probe derived from the coding translated region of the bovine genomic CD14 fragment by PCR (details are provided below in the section describing the preparation of baculovirus recombinant expression vector with bovine CD14 fragment). The probe was labeled with $^{32}$P by random hexanucleotide-primed second strand synthesis (Oligolabelling Kit, Pharmacia Biotech). Screening procedures were performed under conditions of high stringency (0.1×SSC, 1%SDS, 65° C. for 3 hours). One of the clones obtained (ExCeII/BoCD14-1), contained a 1.4 kb insert, which was subcloned into pBluescript SK+, and sequenced using pBS/BoCD14 subclones containing progressive overlapping unidirectional deletions (Nested Deletion Kit, Pharmacia).

This bovine CD14 cDNA clone consists of 1327 bp. An ATG initiation codon is followed by an open reading frame of 1116 nt, and a TAA stop codon at nucleotide 1202. The open reading frame is flanked by 82 bp of 5' untranslated sequence and 122 bp of 3' untranslated sequence. A polyadenylation signal, 5'-ATTAAAA-3', is located 105 bp 3' of the termination codon.

Alignment of bovine CD14 genomic and cDNA sequences reveals that they are colinear from the start of 5' cDNA until the first and only intron (88 bp) winch is found immediately after the ATG initiation codon. The remainder of the coding sequence is uninterrupted. Thus, the intron-exon organization previously described for human and mouse CD14 is precisely conserved in bovine CD14. Comparison of the translated nucleotide sequence of bovine CD14 cDNA with those of human and mouse CD14 cDNAs revealed 74.2% and 62.6% nucleotide identity in coding regions, respectively (FIG. 6).

The primary structure of the bovine CD14 protein was deduced from cDNA sequence, and consists of 374 amino acids. The first methionine is followed by a stretch of hydrophobic and/or neutral residues, typical of eukaryotic signal peptides. Alignment of the amino acid sequences of bovine CD14 with human and mouse CD14 reveals 73.1% and 62.3% identity, respectively (FIG. 7). There are three potential N-linked glycosylation sites (Asn-X-Thr/Ser) all of which are conserved in human and mouse CD14. Moreover, bovine CD14 contains 10 leucine-rich repeating motifs (LXXLXL), common to both human and mouse CD14 (J. Immunol. 145:331, 1990).

Expression of Recombinant Bovine CD14 in Insect Cells

In preparing DNA fragments for producing recombinant CD14 proteins, full length fragments of CD14 translated regions were generated by PCR. Specific sets of PCR primers were designed based on sequence information obtained from bovine CD14 cDNA. The PCR primer for the 5' end contained: two recognition sequences for NheI; a Kozak sequence; an ATG initiation codon; and the first 17–21 nucleotides of translated coding region. The PCR primer for the 3' end contained: two recognition sequences for NheI; and the last 21–24 nucleotides of translated coding region up to and excluding the TAA stop codon (FIG. 8A).

The bovine CD14 translated region was amplified using the 7.1 kb EcoRI-XhoI genomic CD14 fragment (see above) as a template. PCR was carried out using Pwo DNA polymerase (Boehringer). Amplification was done by adding 5 ng of template DNA, 10 mM Tris-HCl pH 8.85, 25 mM KCl, 5 mM $(NH_4)_2SO_4$, 2 mM $MgSO_4$, 250 mM of each dNTP, 250 nM of each primer, and 5 units of Pwo DNA polymerase, in a final volume of 100 μl. The samples were amplified for 30 cycles at 70° C. annealing temperature using a DNA Thermal Cycler (Perkin Elmer).

Amplified fragments were digested with NheI, and individually subcloned downstream of the polyhedrin promoter in the baculovirus transfer vector pETL-HA (C. Richardson, OCI/Amgen). This vector is derived from pETL (Methods in Molecular Biology 39:161, 1995), and contains a 3' 30 bp NheI-BamHI DNA fragment encoding a nonapeptide derived from influenza hemagglutinin (HA), followed by the stop codon TAG (5'-TAC CAA TAC GAT GTT CCA GAT TAC GCT TAG-3')(SEQ ID NO:13). The recombinant transfer vectors were individually cotransfected with the wild-type baculovirus Autographa californica nuclear polyhedrosis virus (AcMNPV, Linear Transfection Module, Invitrogen) into Sf9 cells (Methods in Molecular Biology 39:161, 1995). The recombinant baculovirus clones were selected and purified according to established protocols (Methods in Molecular Biology 39:161, 1995). Sf9 cells were infected with recombinant baculovirus at a multiplicity of 5–10:1.

Figure 9:
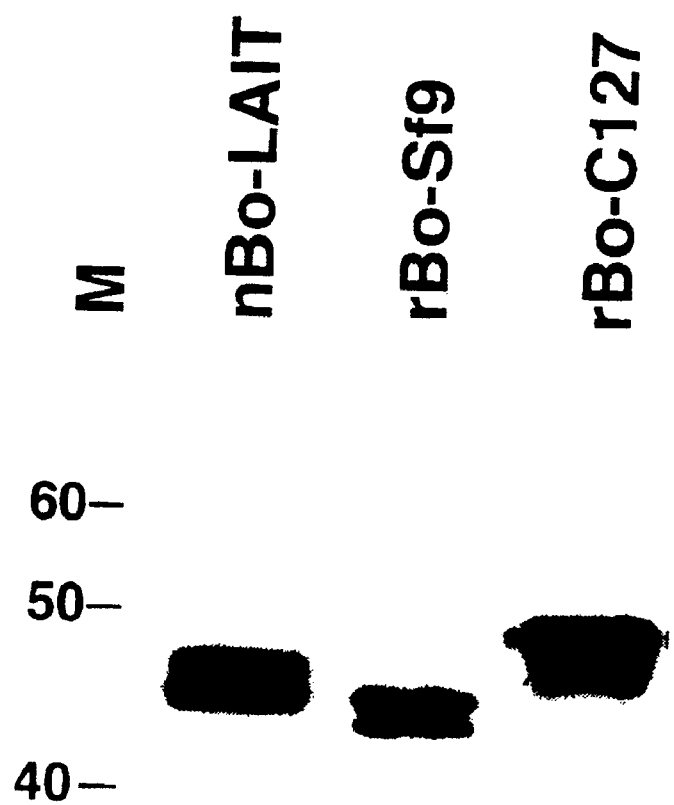
FIG. 9 shows immunoblotting of native and recombinant bovine CD14. Western blot analysis was used to evaluate and compare the sizes of nBo-LAIT protein with recombinant CD14 proteins. 250 ng of CD14 proteins were olectrophoresed on 12.5% SDS-polyacrylamide gel and electrophoretically transferred to PVDF membrane (Millipore) at 180 mA for 30 minutes. The membrane was blocked for 1 hour in 5% skim milk in TBST (20 mM Tris.HCl, pH 7.5, 150 mM NaCl, 0.025% Tween 20), followed by incubation for 1 hour with rabbit anti-Bo-LAIT #842 Ab at concentration 2.5 µg/ml in TBST supplemented with 5% skim milk. The blot was rinsed three times for 10 minutes/rinse in TBST. Goat anti-rabbit IgG conjugated with horse radish peroxidase (BioRad) was used to detect rabbit antibody. The membrane was then rinsed three times (10 minutes/rinse) with TBST. The ECL kit (Amersham) was used to visualize the proteins. Lane 1; MW markers; lane 2; nBo-LAIT-842-Sepharose(TM) affinity purified nBo-LAIT protein; lane 3; rBo-Sf9-12CA5 affinity purified, Sf9 insect cell derived recombinant bovine CD14; lane 4; rBo-C127-842-Sepharose(TM) affinity purified, C127 mouse mammary tumor cell line derived recombinant bovine CD14.

A time course analysis was performed to determine the optimum time period required for the infected Sf9 cells to secrete recombinant CD14 proteins. Immunoblot analysis of the cell media taken at different time points using the anti-HA monoclonal antibody 12CA5 (Cell 57:787, 19841, revealed that the expression of recombinant CD14 proteins reached the maximum level at 96 hours. This period was chosen in subsequent experiments for the production of recombinant proteins for bioassay (see below). Western blot analysis of Sf9 derived recombinant bovine CD14 is illustrated in FIG. 9.

Expression of Recombinant Bovine CD14 in Mammalian Cells

We used a modified version of the pBPV Episomal Mammalian Expression Vector (Pharmacia) for stable expression of recombinant bovine CD14 in mammalian cells. To enable direct selection of transformed cells, pBPV was modified by including a neomycin resistance gene, which was inserted 3.4 kb upstream of the expression cassette. Towards this end, a 1.95 kb HindIII-XbaI fragment from pBCMGSneo (Eur. J. Immunol. 18:98, 1988) was subcloned into pCRII (Invitrogen). The recombinant construct, pCRII-neo, was purified, and the cloned fragment was amplified by PCR. PCR primers were designed such that the recognition sequence for SalI was included at both the 5' and 3' ends. Primer sequences were complementary to the polylinker region of PCRII vector, flanking the HindIII (Primer A) and XbaI (Primer B) cloning sites.

Primer A: 5'-GCA GTC GAC ACT ATA GAA TAC TCA AGC-3' (SEQ ID NO:14)

Primer B: 5'-TTC GTC GAC ATT GGG CCC TCT AGA-3' (SEQ ID NO:15)

The final product was digested with SalI, gel purified, and subcloned into the SalI cloning site of pBPV in the same transcription orientation as that of the contained expression cassette. Plasmid preparations of the modified expression vector, pBPVneo-13, were generated (Plasmid Maxi Kit, Quiagen).

A DNA fragment encoding the translated region of bovine CD14 was prepared by PCR amplification of the gene in the pETL-HA vector. The 5' end PCR primer used in the amplification reaction included: an Xho I recognition sequence; followed by an Nhe I recognition sequence (present in the pETL-HA vector); a Kozak sequence; an ATG initiation codon; and the first 11 to 13 nucleotides of the translated region. The core PCR primer for the 3' end contained the HA coding sequence which was extended, as for the 5' sequences, with the inclusion of an Xho I recognition sequence. Primers are shown in FIG. 8B.

PCR was carried out using Pwo DNA polymerase (Boehringer Mannheim). Amplifications were done by adding 5 ng of DNA template, 10 mM Tris-HCl pH 8.85, 25 mM KCl, 5 mM $(NH_4)_2SO_4$, 2 mM $MgSO_4$, 250 mM of each dNTP, 250 nM of each primer, and 5 units of Pwo DNA polymerase in a final volume of 100 μl. The samples were amplified for 30 cycles at 70° C. annealing temperature using a DNA Thermal Cycler (Perkin Elmer).

The amplified fragments were digested with Xho I and gel purified. These fragments were then subcloned into pBPVneo-13 downstream of the mouse metallothionein I promoter. Prior to the subcloning, pBPVneo-13 was pre-treated with the appropriate restriction enzyme, and dephosphorylated using calf intestinal phosphatase. Recombinant plasmids were prepared using a Plasmid Maxi Kit (Quiagen).

The recombinant plasmid (pBPVneo13-BoCD14) was transfected into the mouse mammary tumor cell line, C127 (PNAS 78:2727, 1981), using 20μg of DNA/$10^7$ cells. DNA transfer was achieved by electroporation at 960 μF/280V using a Gene pulser (Bio-Rad Laboratories). Stable transformants were selected in the presence of 1.5 mg/ml G418 (Life Technologies).

Transfectants expressing high levels of membrane CD14 (non transfected C127 are negative for CD14) were enriched by immunofluorescence staining followed by fluorescence activated cell sorting using a Becton Dickinson FACStar Plus. The level of membrane expression of the exogenous protein correlated well with the amount of secreted CD14 rescued in 48 hour supernatants of confluent cultures of transfected C127 cells. Unlike the purification of recombinant material generated in insect cells, it was not found possible to affinity purify C127 derived material using 12CA5-Sepharose(TM) affinity columns. This might have been due to the loss of the C-terminal HA tag on recombinant proteins derived from C127 cell. As a consequence, recombinant bovine CD14 derived from C127 was affinity purified on 842-Sepharose(TM), Immunoblot analysis of recombinant bovine CD14 derived from C127 cells is illustrated in FIG. 9.

Comparative Growth and Differentiation Promoting Activities of nBo-LAIT and LPS

Figure 10:
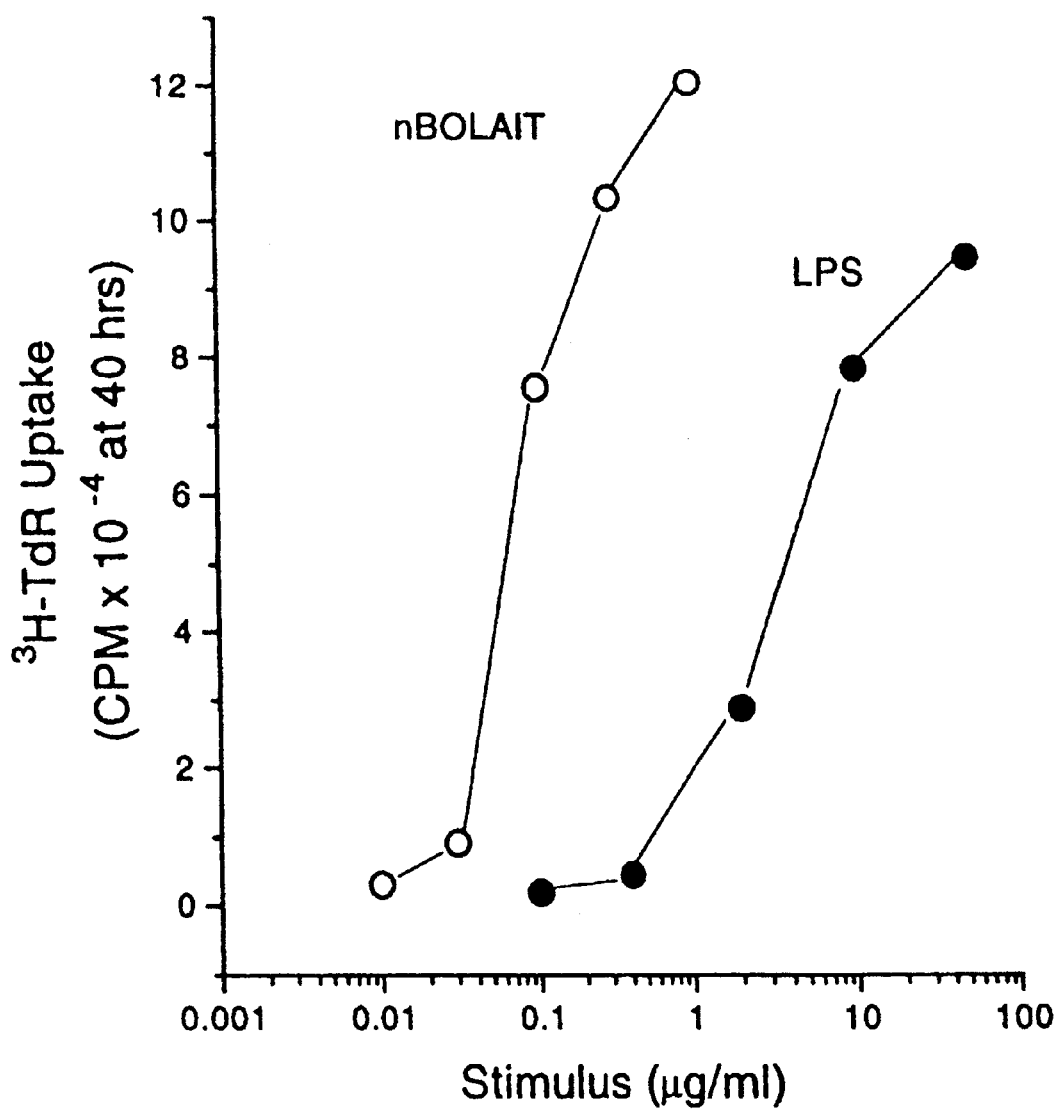
FIG. 10 shows comparative growth promoting activity of nBo-LAIT and LPS. High buoyant density resting murine splenic B cells were prepared, cultured, and harvested as described for FIG. 1A. The indicated concentrations of either affinity purified nBo-LAIT, (affinity purified as described for FIG. 1) or LPS, derived from S. typhosa (Difco), were added at the initiation of culture.

The results shown in FIG. 10 illustrate that native Bo-LAIT supports the growth of high buoyant density, resting, murine splenic B cells with efficiencies roughly 200-fold higher than that of LPS. Thus, nBo-LAIT at 50 ng/ml results in the induction of DNA synthesis comparable to that observed in the presence of 10 μg/ml of LPS.

Figure 11:
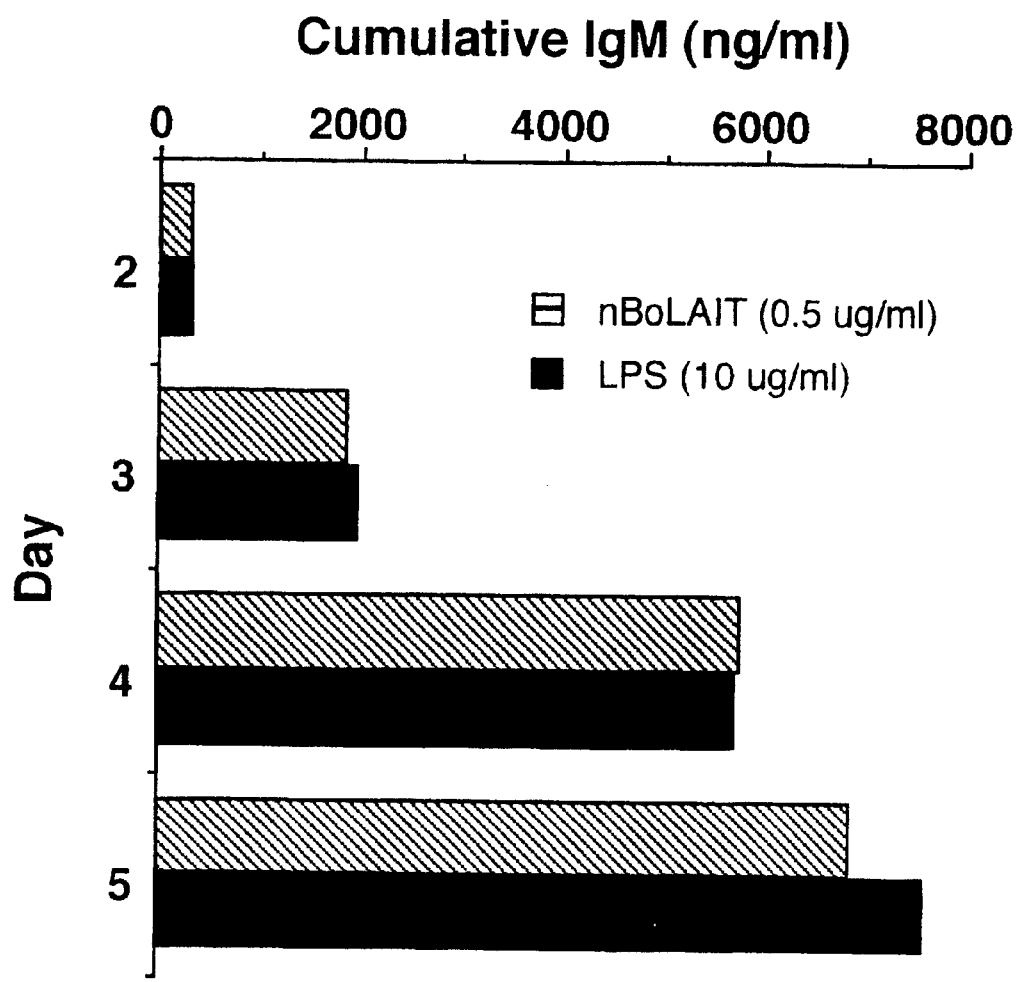
FIG. 11 shows comparative differentiation promoting activity of nBo-LAIT and LPS. High buoyant density, resting, murine splenic B cells were prepared and cultured as described for FIG. 1A. Replicate cultures were initiated using 10 µg/ml of LPS [S.typhosa (Difco)], or 500 ng/ml of affinity purified nBo-LAIT, and harvested at the indicated times. Cumulative IgM production was assessed by quantifying IgM present in supernatants using a commercially available ELISA kit.

The capacity of nBo-LAIT to induce B cell growth is paralleled by its capacity to induce the differentiation of high buoyant density, resting, murine B cells to immunoglobulin secretion. As illustrated in FIG. 11, the amount of cumulative IgM induced by 500 ng/ml of nBo-LAIT is comparable to that induced by 10 μg/ml of LPS. The amount of IgM secretion within a 24 hour culture period was assessed. 500 ng/ml of nBo-LAIT induced 956±10 ng/ml; 754±8.7 ng/ml; and 25±1.4 ng/ml of IgM within the 24 hour culture periods of 48–72 hours; 72–96 hours; and 96–120 hours, respectively. Corresponding values derived from cultures stimulated with 10 μg/ml of LPS were: 1442±71 ng/ml; 874±32 ng/ml; and 183±3 ng/ml, respectively. Thus, nBo-LAIT has the capacity to induce high buoyant density, resting murine B cells to immunoglobulin secretion at rates comparable to those observed when the B cells are stimulated with the most potent stimulus currently known. Further, it has the capacity to do so at concentrations of 1–10% of that of LPS.

The capacity of nBo-LAIT to induce isotype switching of murine resting B cells was also assessed. The supernatants derived from the cultures described above were also assessed for the presence of IgG isotypes. It was observed that 500 ng/ml of nBo-LAIT and 10 μg/ml of LPS induced cumulative levels (ng/ml at day 5) of IgG1: 7.0±0.1 and 5.6±0.6; IgG2a: 358±3 and 406±8; IgG2b: 8±1 and 11±2; IgG3: 75±5 and IgA: 6.5±1.5 and 5.0±0.3, respectively. Thus, nBo-LAIT, has the capacity, to induce some isotype switching by resting murine B cells in the absence of T cells.

Comparative Growth Promoting Activies of nBo- and rBo-LAIT Proteins

Figure 12:
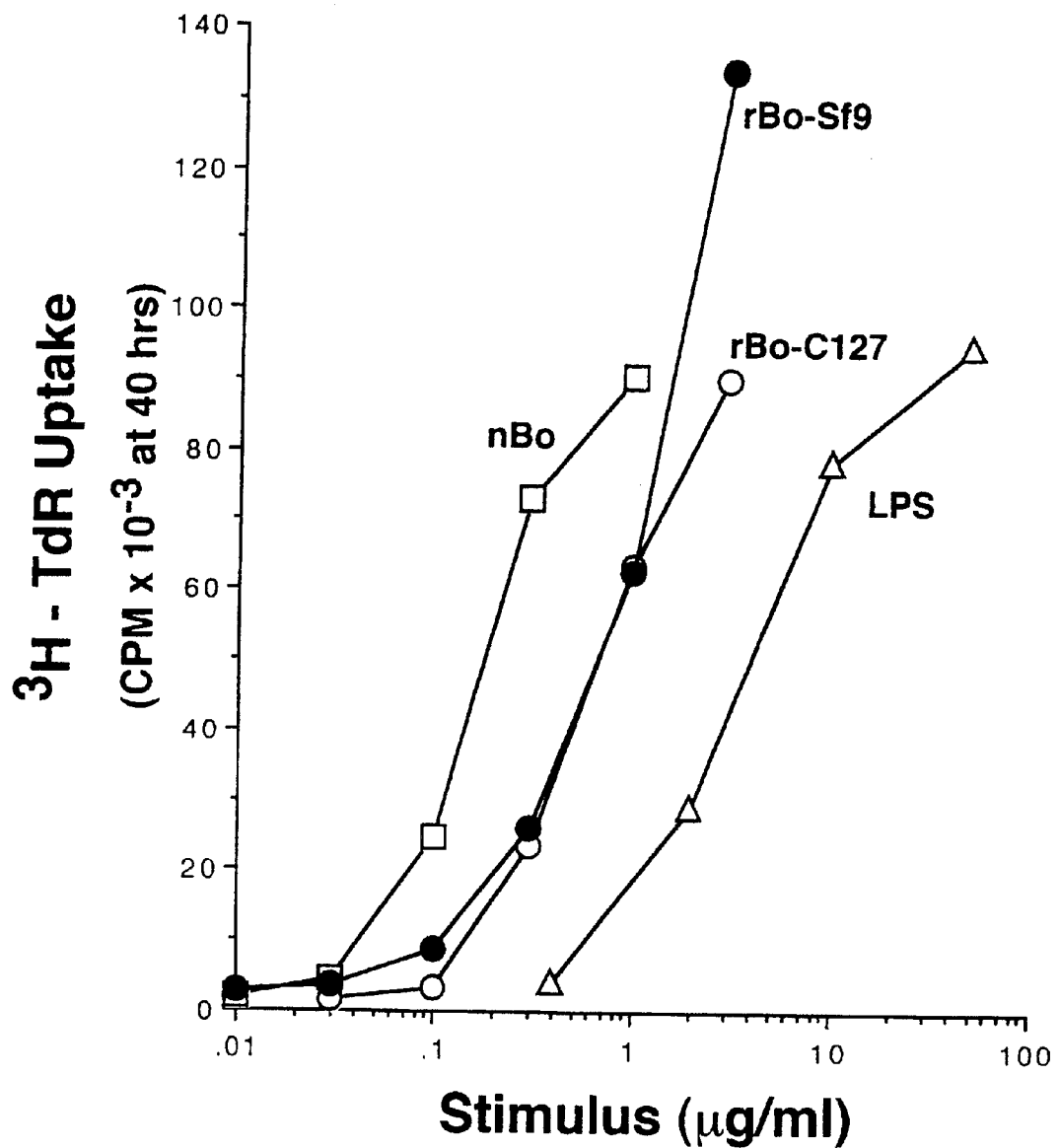
FIG. 12 shows comparative growth promoting activity of nBo- and rBo-LAIT proteins with that of LPS. High buoyant density, resting, murine splenic B cells were prepared, cultured, and harvested as described for FIG. 1A. The indicated concentrations of nBo-LAIT (purified as described for FIG. 1A), rBo-LAIT generated in either insect cells, or mammalian cells, and LPS [S.typhosa (Dlfco)] were added at the initiation of culture. Recombinant Bo-LAIT derived from insect cells was affinity purified from culture supernatants of Sf9 cells transfected with Bo-LAIT cDNA. The expression vector included a 3' 27 mer encoding a nonapeptide derived from influenza hemagglutinin (HA tag). Affinity purification was achieved by passing Sf9 supernatants over Sepharose(TM) conjugated with the mAb 12CA5 (Cell 57:787, 1984), which recognizes the HA tag. Affinity purification of recombinant Bo-LAIT derived from the mammalian expression system, C127, was achieved as for nBo-LAIT, using Sepharose(TM) conjugated with IgG isolated from the polyclonal antiserum derived from rabbit 842.

Recombinant forms of bovine CD14, both those derived in insect cells and mammalian cells, have the capacity to induce the growth of high buoyant density, resting, murine B cells. As illustrated in FIG. 12, rBoCD14 derived from insect cells, and affinity purified on 12CA5-Sepharose(TM), induces robust DNA synthesis at 0.2–3 μg/ml concentrations. Comparable activity was supported by recombinant material derived from the mammalian expression system, and both recombinant forms support B cell growth at ng/ml concentrations, comparable to the activity observed for colostrum derived nBo-LAIT.

Assurance that the bioactivity mediated by nBo-LAIT isolated from bovine colostrum either by classical protein fractionation techniques, or affinity purification, is mediated by the observed protein, comes from the assessment of the bioactivity mediated by recombinant bovine CD14. As illustrated in FIG. 9, the apparent molecular weights of neither of the recombinant forms of bovine CD14 are identical to that of nBo-LAIT. The reason for the observed differences in apparent molecular weight is not clear but might be due to either distinct co- and/or post-translational modifications, distinct sizes of the core proteins, or both. Monocyte derived soluble CD14 has been documented and can be generated in one of three currently understood mechanisms, each of which would result in proteins of distinct molecular weight. It can be secreted as a full length molecule (Eur. J. Immunol. 23:2144, 1993; Eur. J. Immunol. 25:604, 1995), the membrane expressed GPI linked form can be cleaved by phospholipases (J. Immunol. 141:547, 1988; EMBO J. 13:1741, 1994), and the membrane expressed GPI linked form can be cleaved by serine/threonine proteases, putatively expressed on the outer plasma membrane of the monocyte it self, and activated in as yet uncharacterized ways (J. Immunol. 147:1567, 1991). It remains to be determined whether the distinct apparent molecular weights of rBo-LAITs and colostrum derived nBo-LAIT is due to distinct co- and/or post-translational modification of the recombinant materials supported by their respective expression systems, or distinct core protein sizes, or both.

Growth Promoting Activity of nBo-LAIT is B Cell Specific

Having observed the bioactivities of nBo-LAIT on murine B cells, effects on the physiology of murine T cells was examined. The fact that isolated purified B cells do respond to nBo-LAIT does not preclude the possibility that Bo-LAIT can also activate T cells.

Figure 13:
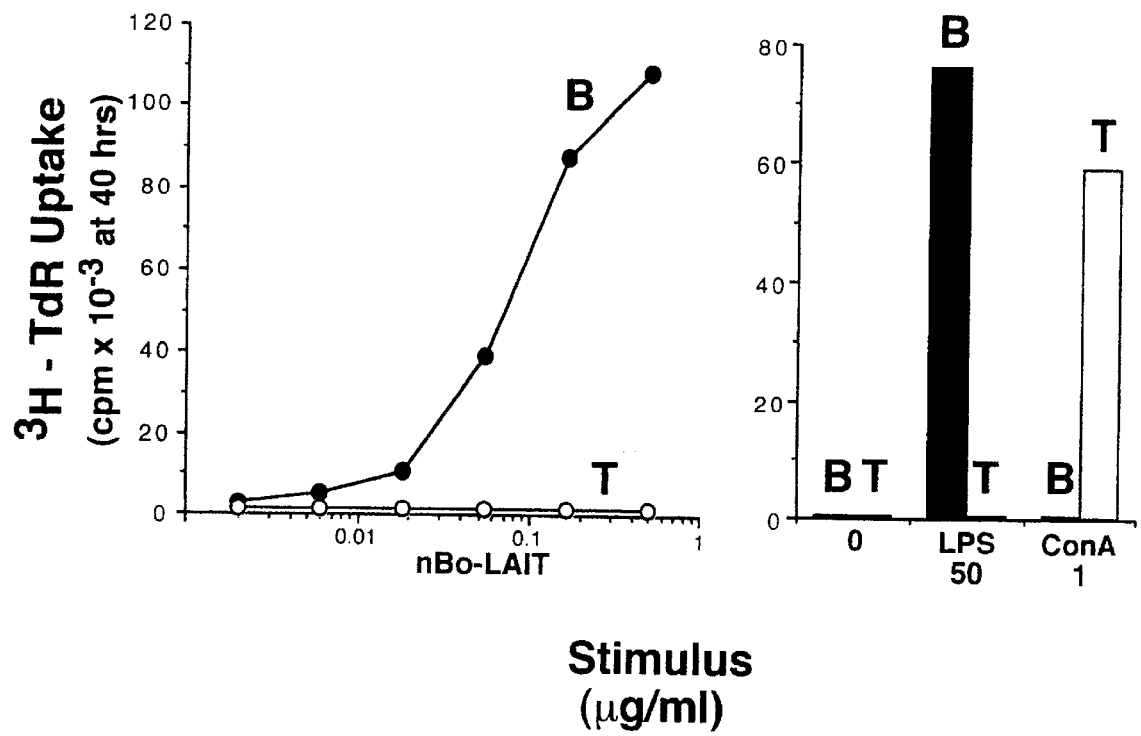
FIG. 13 shows a comparative analysis of the growth promoting activity of nBo-LAIT on purified primary B and T cell populations. High buoyant density, resting, murine splenic B cells were prepared as described for FIG. 1A. Primary T cells were isolated from the lymph nodes of the same animals from which the splenic B cells were isolated. Specifically, lymph node suspensions were passed over anti-Ig columns (Biotex Labora) according to manufacturers instructions, and as previously described (Eur. J. Immunol. 24:967, 1994. T cell populations were >95% $CD3^+$, and <0.5% $mIg^+$, as assessed by immunofluorescent staining and FACS analysis. The left panel shows the proliferative response of cultures containing $1.5 \times 10^5$ purified T or B cells in response to the indicated concentrations of affinity purified nBo-LAIT. The right panel shows the proliferative response of the same number of B or T cells to either 50 µg/ml of LPS [S.typhosa (Difco)] or 1 µg/ml of Concanavalin A (Sigma). Serum free conditions were employed, and all stimuli were added at the initiation of culture. At 40 hours, cultures were pulsed with 1 µCi of $^3$H-TdR, harvested onto filter discs 6 hours later, and thymidine uptake assessed by scintillation spectroscopy. Numbers indicated represent the average cpm of duplicate cultures.

Lymph node T cells were isolated by negative selection on anti-Ig columns (Biotex Labora) as previously described (Eur. J. Immunol. 24:967, 1994). The resuting effluent population contained >95% $CD3^+$ cells and >0.5% $mIg^+$ cells as assessed by immunofluoresence staining and FACS analysis. High buoyant density splenic B cells were isolated from the same mice, and both the lymph node T cells and splenic B cells assessed for their responsiveness to nBo-LAIT. The purity of these populations was assessed functionally by analyzing their responses to the B cell specific mitogen LPS, and the T cell specific mitogen, concanavalin A (ConA). As illustrated in the right panel of FIG. 13, the B cells, but not the T cells responded with robust DNA synthesis to LPS, while the T cells, but not the B cells responded to ConA. As illustrated in the left panel, the T cells did not respond to nBo-LAIT over the dose range tested, while the B cells responded to nBo-LAIT at concentrations of 10 ng/ml and higher.

LAIT-protein Induced B Cell Growth and Fetal Bovine Serum

It has been demonstrated recently that monocytes respond to soluble CD14 (sCD14) isolated from the urine of nephrotic patients with the production of pro-inflammatory cytokines (Eur. J. Immunol. 24:17790, 1994), in the absence of serum derived lipopolysaccharide binding protein (LBP). In contrast, the capacity of low concentrations of LPS to stimulate the production of these same cytokines by CD14 expressing monocytes is serum dependent (J. Exp. Med. 176:719, 1992). This serum dependence is overcome at high concentrations of LPS. Thus, cytokine production by monocytes induced by 10 ng/ml LPS is strictly dependent on serum/LBP, but that induced by 50 µg/ml LPS is not.

Figure 14:
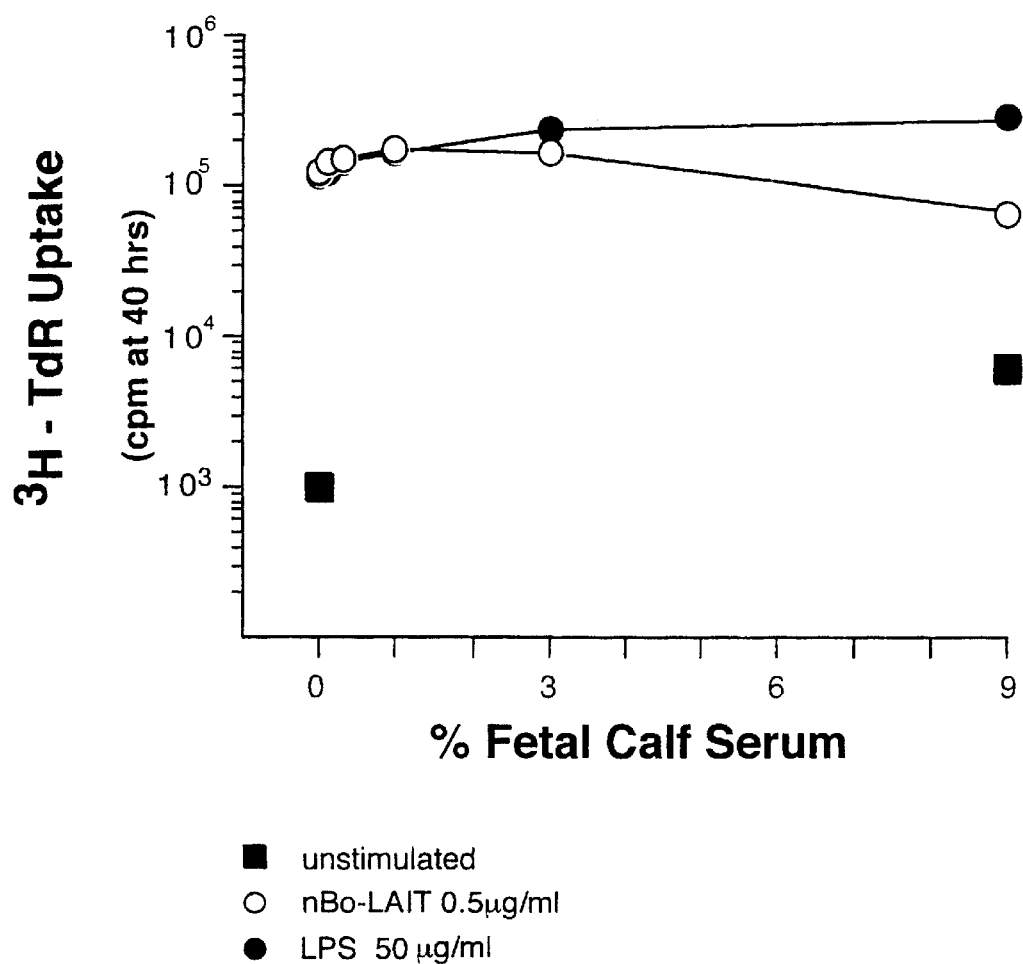
FIG. 14 shows the fetal calf serum independence of nBo-LAIT mediated murine B cell growth. High buoyant density, resting, murine splenic B cells were prepared, cultured, and harvested as described for FIG. 1A. Serum free culture medium was supplemented with the indicated concentration of heat inactivated (56° C. for 1 hour) fetal calf serum (Gibco BRL) and either no stimulus (■), 0.5 µg/ml affinity nBo-LAIT (○), or 50 µg/ml LPS [S.typhosa (Difco)] (●). At 40 hours, cultures were pulsed with 1 µCi of $^3$H-TdR, harvested onto filter discs 6 hours later, and thymidine uptake assessed by scintillation spectroscopy. Numbers indicated represent the average cpm of duplicate cultures.

To determine whether the presence of fetal bovine serum LBP would affect the capacity of low concentrations of nBo-LAIT to induce the growth of high buoyant density murine B cells, the response elicited by 500 ng/ml nBo-LAIT was assessed over a broad range of FBS concentrations, in comparison to that induced by 50 µg/ml LPS. As illustrated in FIG. 14, the B cell responses to both these stimuli were unaffected by the presence of up to 9% FBS present in the culture medium.

LAIT-protein Induced B Cell Growth and mCD14

The diffential sensitivity of B cells and monocytes to LPS mediated activation could be related to the expression of membrane CD14 (mCD14) by the latter. It has been directly demonstrated that the sensitivity of LPS mediated activation can be dramatically enhanced by the presence of mCD14 on responding cells. Specifically, it has been demonstrated that the sensitivity of a mCD14 negative pre-B cell line to LPS is increased by roughly a thousand-told upon the forced expression of exogenous GPI linked mCD14 (J. Exp. Med. 175:1697, 19921. Whether primary B cells express mCD14 remains contentious. The high specific activity of Bo-LAIT relative to that of LPS in B cell activation is consistent with its mode of activation being independent of mCD14 expression.

To directly assess the involvement of mCD14 expression in Bo-LAIT mediated B cell activation, the presence of CD14 specific mRNA was assessed in the high buoyant density murine B cell populations used as responders. Total RNA from $10^7$ cells from each of three spleen derived populations: unfractionated splenocytes; T-depleted, Percoll fractionated, high buoyant density cells, those used routinely in LAIT-protein mediated growth assays; and membrane Ig expressing cells isolated from the high buoyant density T-depleted population by immunofluorescence labelling with FITC conjugated rat mAb specific for mouse Igκ [187.1 (Hybridoma 1:5, 1981)] and subsequent purification using a Becton Dickinson FACStar Plus cell sorter. As illustrated in FIG. 15, these three populations contained 59.2%; 83.5%; and 99.8% mIg$^+$ cells. Isolated RNA from these populations was resolved on a 1.2% formaldehyde gel, and transferred to a nylon membrane (GeneScreen), crosslinked, prehybridized, and hybridized with two probes, sequentially.

The mouse CD14 probe was derived by PCR from genomic DNA. Specifically, amplification was done by adding Pwo DNA polymerase (Boehringer Mannheim) to 0.4 µg of Balb/c genomic DNA with the forward primer: 5'-CTA GAA TTC TCT CCC GCC CCA CCA GAG CCC TGC G-3' (SEQ ID NO: 11); and reverse primer: 5'-CTA GAA TTC TTA AAC AAA GAG GCG ATC TCC TAG G-3' (SEQ ID NO: 12). The sample was amplified for 30 cycles in a DNA thermal cycler (Perkin Elmer) using an annealing temperature of 55° C. The amplified fragment was resolved by agarose gel electrophoresis, excised from the gel, and purified. An L32 probe (Nucl. Acid. Res. 16: 10751, 1988) was used to normalize RNA loading. Each probe (100 ng) was labelled using an oligolabelling kit (Pharmacia) to a specific activity of 0.2–1×10$^9$ cpm/µg DNA. Membranes were probed and washed in 0.2×SSC, 1% SDS at 65° C. for 2 hours, and exposed.

As illustrated in FIG. 15, RNA derived from both the unfractionated splenocytes, and the T-depleted high buoyant density splenocytes contained CD14 specific mRNA, while the FACS purified B cells did not. The CD14 signal in the T-depleted, high buoyant density splenocytes, heretofore referred to as resting B cells, is likely due to contaminating monocytes, as these populations are 85–90% mIg$^+$, but >98% MHC Class II$^+$ as assessed by immunofluoresence staining and FACS analysis. It is therefore possible that Bo-LAIT mediated growth of B cells in this population is indirect, and is mediated through the activation of contained monocytes.

The response of T-depleted, Percoll fractionated splenocytes, and FACS purified mIg$^+$ cells derived from this population to nBo-LAIT, and LPS induced growth was compared. As illustrated in FIG. 16, both populations responded robustly to both stimuli. The 10-fold higher stimulation indices obtained with 99.8% pure B cell populations was due to the reduced non-stimulated background observed in these cultures (FIG. 16).

LAIT-protein Induced B Cell Growth and CD40

As described above, mAbs specific for CD40, which is expressed on the membrane of B cells, have been observed to induce growth of murine B cells (Sem. in Immunol. 6:267, 1994; PNAS 83:4494, 1986; J. Immunol. 140:1425, 1988;).

To determine whether there is some relationship between anti-CD40 and LAIT-protein induced B cell activation, the capacity of rBo-LAIT to stimulate the growth of high buoyant density splenic B cells isolated from either conventional C57BL/6 mice or C57BL/6 mice in which CD40 expression was ablated through targeted gene disruption was examined (Immunity 1:167, 1994). As illustrated in FIG. 17, no differences in the responses of these B cells were observed over the concentration range of rBo-LAIT tested.

These results indicate that CD40 per se need not be involved in LAIT-protein signalling, but the possibility that second messenger generating systems utilized by CD40 and the putative membrane receptor for LAIT-protein are shared, cannot be excluded.

Comparative Analysis of Native Human, Bovine and Murine CD14

Having observed the activities of nBo-LAIT and rBoCD14 on murine B. cells, the activities of mouse CD14

(Mo) and human CD14-(Hu) isolated from fluids other than colostrum were examined. It has been demonstrated that Hu-CD14 is present in the urine of nephrotic patients (Eur. J. Immunol. 24:1779, 1994). Hu-CD14 was isolated using a modified protocol. Urine was precipitated by adding saturated $(NH_4)_2SO_4$ to a final concentration of 45% (v/v), and precipated material cleared by centrifugation at 14000 g for 30 minutes. $(NH_4)_2SO_4$ concentration in the supernatant of this spin was then increased to 75% (v/v). The precipitate was pelleted at 14000 g for 30 minutes, and solubilized in TN buffer pH8.0 containing 10 mM Tris, 150 mM NaCl, and "Complete" protease inhibitor cocktail (Boehringer Mannheim). Insoluble material was cleared by centrifugation at 13000 g for 15 minutes. The supernatant of this spin was desalted on G-10 columns (Bio Rad) equilibriated in TN buffer pH8.0. This material was then passed over Sepharose 4B to which the human CD14 specific mAb, 3C10 (J. Exp. Med. 15:126, 1983), had been conjugated. Bound material was eluted in 100 mM acetate, 150 mM NaCl, pH2.8, and immediately neutralized by adding a tenth volume of 1M Tris, pH 8.0. The eluate was concentrated in a speed-vac, and protein concentration determined calorimetrically.

Murine CD14 was isolated from the supernatant of the mouse hybridoma OKT3 (PNAS USA 77:4914, 1980). During a screening analysis of cell populations for the expression of CD14 specific mRNA, it was observed that every hybridoma assayed contained message. It follows that if the donor and fusion partner were both of murine origin, the CD14 produced would also be of murine origin. The hybridoma OKT3 satisfies these criteria. To assess whether CD14 protein was being produced by OKT3, and in sufficient quantities to allow isolation, material contained in 1 liter of OKT3 culture supernatant was affinity purified on 3C10-Sepharose as described above for humane urine derived CD14. The specificity of 3C10 has been mapped to residues 7–10 of human CD14 (J.Biol. Chem. 270:361, 1995). These residues are highly conserved in bovine and murine CD14.

The left panel of FIG. 18 illustrates a comparative silver staining analysis of 1 µg each of affinity purified human urine CD14 (nHu), colostral bovine CD14 (nBo), and OKT3 derived mouse CD14 (nMo). The right panel of FIG. 18 illustrates a comparative immunoblot analysis of 250 ng of each of the same three species of CD14, probed with mAb 3C10. As illustrated, the purity of all three preparations was comparable, as was their reactivity with mAb 3C10.

Apparent discrepancies in the molecular weights of CD14 of the three species with the differences in the number of amino acids encoded by their respective cDNAs could be due to co- and/or post-translational modification. In this context, it is apparent that mouse, human, and bovine CD14s contain five, four and three potential N-glycosylation sites respectively.

The capacity of these three CD14 preparations to stimulate murine B cell growth was assessed. As illustrated in FIG. 19, CD14 isolated from the three species had comparable specific activity, and was active in the ng/ml concentration range. The results also demonstrate that isogenic material is functional, specifically, murine CD14 can stimulate murine B cells. The results also demonstrate that colostral CD14 is not peculiar in its capacity to stimulate B cells, and thus it is not likely a special form of the molecule which is generated in the specialized circumstances of lactation.

Growth Promoting Activity of nBo-LAIT on Human Cord Blood B Cells

Having observed a variety of bioactivities of nBo-LAIT on murine B cells, effects on the physiology of human B cells were examined. Two sources of B cells were utilized. Since one possible role of LAIT-protein is involvement in potentiating the development of the neonatal immune system, its capacity to stimulate the growth of B cells derived from the neonate, specifically, those isolated from cord blood was assessed.

Cord blood was diluted 1:1 in phosphate buffered saline (PBS), and overlayed onto Percoll (Pharmacia), ρ=1.077. The gradient was centrifuged as described in connection with FIG. 1A. The ρ=1.077/1.000 interface was harvested and washed twice in PBS supplemented with 5% fetal bovine serum (FBS). The resulting leukocyte preparation was then stained with fluorescein conjugated mAb specific for the B cell membrane marker CD72. CD72 positive cord leukocytes were then positively selected by FACS, resulting in purities of >98%. These positively selected B cells were then cultured in serum free defined medium, as for murine B cells. The only difference in the growth assays for murine and human B cells, was that the latter were pulsed with thymidine at 60 hours, for 12 hours, rather than at 40 hours, for 6 six hours.

As illustrated in FIG. 20A, nBo-LAIT acts with mAbs specific for Igκ and Igλ in its capacity to induce the growth of neonatal B cells. While both immobilized (plate bound) anti-light chain mAbs and 2 µg/ml nBo-LAIT induce an increase in thymidine uptake over background, individually, the combination of the two supported a further 5-fold increase.

These results indicate that it might be possible that LAIT protein consumed by the breast fed neonate functions as a T cell surrogate in aid of stimulating B cells which have encountered antigen to grow and differentiate into Ig secreting cells, in the absence of a fully developed T cell compartment (J. Exp. Med. 169:2149, 1989; Science 245:749, 1989; Intl. Immunol. 2:859, 1990; Intl. Immunol. 2:869, 1990).

CD14 in Human Colostrum and Normal Serum

To determine the concentration of CD14 present in colostrum and normal serum, colostral samples from two donors, and serum samples from five healthy donors, were assayed for the presence of CD14 using a specific ELISA (IBL-Hamburg). As shown in Table 3, serum from this cohort of healthy individuals contained CD14 concentrations ranging from 1.7–3.2 µg/ml, and was gender independent. These values correspond well with those reported by Grunwald et al. (J. Immunol. Method 155:225, 1992).

TABLE 3

| DONOR | GENDER | µg/ml* |
| --- | --- | --- |
| A. M. | F | 2.8 |
| N. J. | F | 2.7 |
| M. J. | M | 1.7 |
| E. K. | M | 2.9 |
| A. D. | M | 3.2 |

*2.6–3.4 µg/ml according to ELISA kit manutacturer (IBL, Hamburg)

As illustrated in FIG. 21, the CD14 content in colostrum taken at 22 hours post-partum (A.D.), and early breast milk taken at four days post-partum (S.B.), contained roughly 20-fold higher concentrations of CD14 than did normal serum. Multiple samples extending to 78 days post-partum were obtained from one donor (S.B.), and while CD14 concentrations dropped considerably compared to that observed at day 4, they remained roughly 3–5-fold higher than that observed in normal serum, throughout the screening period assayed (FIG. 21).

No information regarding the concentration of serum CD14 in lactating women is yet available. Thus, it remains to be determined whether the high concentrations of CD14 observed in colostrum and breast milk are restricted to these fluids, or reflect a generalized increase in CD14 concentration in all body fluids of lactating women.

It may be that the transient exposure of the neonatal immune system to the B cell tropic growth and differentiation activity of colostral CD14 plays a part in development of the neonatal immune response machinery. The physiological relevance of the presence of this activity in colostrum is consistent with the observation that, as described above, T cell function in the neonate is compromised, possibly due to the presence of high concentrations of TGFβ1 and TGFβ2 in colostrum and early breast milk (J. Cell. Biol. 105:1039, 1987; Cell 49:437, 1987; EMBO J. 6:1633, 1987). As shown in Table 2, submitogenic concentrations of CD14 in combination with submitogenic concentrations of mAb specific for membrane immunoglobulin, supports the activation of B cells. CD14 might function as a T cell surrogate within the developing neonatal immune system. As such, a neonate can benefit from the use of CD14 as an infant formula additive by exposure to its immune-stimulating effects absent from synthetic formula.

Growth Promoting Activity of nBo-LAIT on Human Tonsil B Cells

The bioactivity of nBo-LAIT on B cells isolated from adults was assessed, in isolation, and in combination with immobilized (plate bound) anti-light chain mAbs, to stimulate B cells isolated from human tonsils.

Tonsil B cells were prepared by negative selection. Tonsil leukocytes were prepared as for cord blood leukocytes. The resulting population was labelled with biotinylated mAb specific for CD3ε (Becton Dickenson), followed by labelling with iron containing "micro-beads" (Becton Dickenson). After one wash, the labelled population was passed through a MACS (Becton Dickenson), and the effluent collected. This population contained <1% T cells, and >97% B cells as assessed by immunofluorescence staining with lineage specific mAbs. These B cells were then subjected to further fractionation on Percoll discontinuous density gradients, identical to those used for the isolation of high buoyant density murine B cells. The assays described used those B cells banding at the ρ=1.085/1.079 interface. These negatively selected, density fractionated resting B cells were cultured as described below, pulsed, and harvested as for cord blood B cells.

As illustrated in FIG. 20B, and in contrast to results obtained with B cells isolated from neonates, nBo-LAIT, in isolation, present at concentrations as low as 300 ng/ml stimulated robust growth of these resting tonsil B cells. Further, the response at some concentrations of nBo-LAIT was substantially enhanced when assessed in combination with immobilized anti-light chain mAbs (FIG. 20B).

Mature human B cells are susceptible to the growth promoting activities of nBo-LAIT, which are amplified in combination with simultaneous ligation of the B cell antigen receptor. These results characterize the potential utilization of LAIT-protein in vaccine vehicles, in aid of increasing their adjuventicity, or by possibly reducing the need for adjuvants.

A limitation of vaccination technology is the immunogenicity of a particular antigen preparation. Certain adjuvants are thought to function by recruiting and activating antigen specific T cells. CD14, as a T cell surrogate for antigen specific B cell responses, may provide an improved means to activate antigen specific B cells such that they will not only expand and differentiate into antibody secreting cells, but would, once activated, function as efficient APC for the recruitment of T cells. This would enhance both the propagation of the specific immune response and T cell mediated isotype switching.

T cell immune deficiencies are known. Immunodeficiency states associated with T cell dysfunction due to the lack of expression of gp39 (CD40L) (which maps to the X chromosome) have been characterized: (i) X-linked hyper IgM syndrome (HIM); (ii) common variable immunodeficiency (CVI); and (iii) X-linked agammaglobulinemia (XLA). In some of these disease states (HIM), T cells isolated from patients have been shown to be unable to activate B cells (Science 259:990, 1993), and this phenotype correlates with the absence of functional gp39 (CD40L). In these circumstances, CD14, either targeted for the induction of specific humoral responses, or administered as a polyclonal B cell activator could function to induce/maintain levels of isogenic Ig consistent with protection against the daily barrage of potential environmental pathogens.

The presence of CD14 in colostrum is consistent with its role in stimulating B cells within the suckling neonate. The effectiveness of CD14 in aiding development of neonate immune systems can be evaluated in an animal model.

CD14 deficient females, created through targeted disruption of the CD14 locus, will be mated with either heterozygous, or CD14 deficient males. This will enable the assessment of the effects of the absence of colostral CD14 on B cell development in pups that do, or do not express CD14. Specifically, B cell ontogeny and the accumulated development of serum IgM and IgG levels will be compared, as well as the capacity of these pups to mount specific immune responses.

Further, the role that serum CD14 (sCD14) plays in the maintenance of circulating levels of "natural" IgM can be assessed. Levels of circulating IgG and IgM are under distinct control. Serum IgG is virtually absent in mice reared in an antigen free environment, while IgM levels are unaltered. Towards addressing the potential role of sCD14 in the regulation of serum IgM levels, CD14 sufficient and deficient mice derived from the above matings will be reared gnotobiotically.

Dysregulated expression of sCD14 is associated with the pathology of specific disease states. The level of sCD14 in the serum of patients with rheumatoid arthritis (RA) is elevated (Clin. Exp. Immunol. 91(2):207, 1993). It has also been reported that there is an increase in the number of activated $CD14^+$ monocytes in the synovium of RA patients (Br. J. Rheumatol. 29(2):84, 1990; J.Rheumatol. 22(4):600, 1995). While it remains to be determined whether the level of sCD14 in synovial fluid of RA patients is elevated, $CD14^+$ monocytes, upon activation, express membrane associated proteases which can cleave membrane CD14, resulting in the production of sCD14 (Eur. J. Immunol. 25:604, 1995). Consistent with the capacity of sCD14 to activate human B cells, described herein, the synovial fluid of RA patients contains high frequencies of activated B cells, at least some of which may be producing rheumatoid factor (Clin. Immuno. Immunopathol. 3112):272, 1984; Clin. Exp. Immunol. 55(1):91, 1984). Thus, a paradigm emerges, involving the increased production of sCD14 in RA patients, and its possible involvement in the activation of B cells resulting in the production of rheumatoid factor. Antibody mediated clearance of sCD14 may therefore result in the amelioration of symptoms mediated by dysregulation of B cell activation and rheumatoid factor production in RA patients. Further, antibody mediated clearence of sCD14 would ameliorate inflammation supported by sCD14 induction of pro-inflammatory cytokines by monocytes (Eur. J. Immunol. 24:1779, 1994).

Routine production of human monoclonal antibodies (mAbs) has been difficult for a number of reasons, not the least of which is the inability to enrich for activated human B cells of desired antigen specificity. The capacity of sCD14 to induce human B cells of desired antigen specificity. The capacity of sCD14 to induce human B cell growth and differentiation in vitro, affords its possible utilization in the production of antigen specific mAbs. We show herein that sCD14 at high concentrations (0.5–1 µg/ml) activates human B cells in a polyclonal fashion. However, sub-optimal mitogenic concentrations of sCD14 are shown to synergizc with mAb specific for the B cell receptor for antigen (BcR). Thus, sub-optimal concentrations of sCD14 preferentially activate those B cells which receive a complementary signal through the BcR. The BcR specific mAb functions as an antigen surrogate in these circumstances. If specificity is imposed on the delivery of the BcR signal, the ensuing B cell response would also be specific. Thus, when anti-BcR is replaced by a specific antigen, the synergistic stimulus provided by the simultaneous presence of sCD14 would be focussed on the antigen specific B cells, exclusively. Thus, the ensuing production of antibody would be antigen specific. Populations of B cells activated in this fashion would be highly enriched for activated, antigen specific B cells, and would therefore facilitate the production of human hybridomas secreting mAb of desired specificity.

The effectiveness of CD14 as an adjuvant in vaccination technology can be evaluated using an animal model. Bo- and Hu-CD14 will be modified with the hapten TNP. Haptenated material will be assessed for its capacity to induce polyclonal B cell activation in vitro, to insure that haptenation has not altered CD14 bioactivity. Conjugates will be injected subcutaneously, or intramuscularly, and over time, serum will be assessed for its content of specific antibody. Using another series of mice, draining lymph nodes will be collected, and contained antibody secreting cells enumerated. In addition, some recipients will be immunized with mixtures of varying amounts of CD14 and either protein or cellularantigen. Serum antibody titres, as well as antigen specific, and total Ig secreting cells will be enumerated.

Toxicity of CD14 can be evaluated in acute intravenous studies in mice, rats and monkeys. Acute subcutaneous irritation studies in rats can be performed, as well as in the long term, studies involving multiple subcutaneous and intravenous injections in the three species. Gross pathologic and histopathologic assessment will be performed, as well as serum chemistry and hematological analyses. The genotoxic potential can be assessed in mammalian cells in vitro, and in a mouse micronucleus assay. Teratogenic potential can be assessed in pregant mice, rats, and monkeys.

In administering CD14 to a human subject, conventional pharmaceutical practice can be employed. As an additive to infant formula, it might be added to the formula at the itime of manufacture. It might be prepared as a tablet or capsule, or powder for mixing just prior to administration. In the case of vaccine preparation, it might be included as part of a vaccine prepared according to otherwise standard procedures. Administration could be by any convenient means, for example, intravenous, subcutaneous, intramuscular, intraventricular, intracranial, intracapsular, intraspinal, intracisternal, intraperitoneal, or oral administration.

Parenteral formulations may be in the form of liquid solutions or sususpensions.

Methods known in the art for making formulations can be found in, for example, "Remington's Pharmaceutical Sciences." Formulations for parenteral administration may, for example, contain as excipients sterile water or saline, polyalkylene glycols such as polyethylene glycol, vegetable oils, hydrogenated naphthalenes, etc.

In terms of variation from a native amino acid sequence of CD14, at the very least, conservative substitutions could be made. Conservative substitutions are described in the patent literature, as for example, in U.S. Pat. No. 5,264,558 it is expected, for example, that interchange among non-polar aliphatic neutral amino acids, glycine, alanine, proline, valine and Isoleucine, would be possible. Likewise, substitutions among the polar aliphatic neutral amino acids, serine, threonine, methionine, asparagine and glutamine could possibly be made. Substitutions among the charged acidic amino acids, aspartic acid and glutamic acid, could probably be made, as could substitutions among the charged basic amino acids, lysine and arginine. Substitutions among the aromatic amino acids, including phenylalanine, histidine, tryptophan and tyrosine would also likely be possible. These sorts of substitutions and interchanges are well known to those skilled in the art. Other substitutions might well be possible. Of course; it would also be expected that the greater the percentage of homology of a variant protein with a naturally occurring protein, the greater the retention of metabolic activity.

What is claimed is:

1. A method of manufacturing infant formula which comprises incorporating a polypeptide into the formula, wherein said polypeptide comprises the amino acid sequence of a native mammalian CD14 protein identified as SEQ ID NO:4, SEQ ID NO;5, or SEQ ID NO:6 and which polytentide activates B cells.

2. The method of claim 1, wherein the polypeptide comprises the amino acid sequence identified as SEQ ID NO:4 and is a soluble protein obtained from a mammary secretion of a bovine mammal.

3. Infant formula manufactured according to claim 1.

4. Infant formula manufactured according to claim 2.

5. A method of manufacturing infant formula which comprises incorporating a polypeptide into the formula, wherein said polypeptide comprises the amino acid sequence of a native mammalian CD14 protein identified as SEQ ID NO:4 and which polypeptide activates B cells.

6. A method of manufacturing infant formula which comprises incorporating a polypeptide into the formula, wherein said polypeptide comprises the amino acid sequence of a native mammalian CD14 protein identified as SEQ ID NO:5 and which polypeptide activates B cells.

7. Infant formula manufactured according to claim 5.

8. Infant formula manufactured according to claim 6.

* * * * *

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH: 1122 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO: 1:

| | | | | | |
|---|---|---|---|---|---|
| ATGGTGTGCG | TGCCCTACCT | GCTGCTGCTG | CTGCTGCCGT | CACTGCTGCG | TGTGTCTGCG | 60 |
| GACACAACAG | AACCCTGCGA | GCTGGACGAC | GACGATTTCC | GTTGTGTCTG | CAACTTCACG | 120 |
| GATCCGAAGC | CTGACTGGTC | TAGCGCCGTT | CAGTGTATGG | TTGCCGTCGA | GGTGGAGATC | 180 |
| AGTGCCGGCG | GCCGCAGCCT | GGAACAGTTT | CTCAAGGGAG | CCGACACCAA | CCCGAAGCAG | 240 |
| TATGCTGACA | CAATCAAGGC | TCTGCGCGTT | CGGCGACTCA | AGCTGGGCGC | TGCACAGGTT | 300 |
| CCTGCTCAGC | TTCTGGTCGC | CGTTCTGCGC | GCGCTCGGGT | ACTCTCGTCT | CAAGGAACTG | 360 |
| ACGCTTGAGG | ACCTGGAGGT | AACCGGCCCA | ACGCCCCCGA | CGCCTCTGGA | AGCCGCTGGG | 420 |
| CCTGCGCTCA | CCACCCTCAG | TCTGCGTAAC | GTATCGTGGA | CAACAGGAGG | TGCCTGGCTC | 480 |
| GGCGAACTGC | AGCAGTGGCT | CAAGCCTGGG | CTCAGGGTGC | TGAACATTGC | CCAAGCACAC | 540 |
| TCGCTTGCCT | TTCCGTGCGC | AGGGCTCTCC | ACCTTGAGG | CGCTCACCAC | CCTAGACCTG | 600 |
| TCTGACAATC | CCAGTCTCGG | CGACACGGGG | CTGATGGCAG | CTCTCTGTCC | GAACAAGTTC | 660 |
| CCGGCCCTCC | AATATCTAGC | GCTACGCAAC | GCGGGGATGG | AGACGCCGAG | CGGCGTGTGC | 720 |
| GCGGCGCTGG | CGGCAGCGAG | GGTGCAGCCC | CAAAGCCTGG | ACCTCAGCCA | CAACTCGCTG | 780 |
| CGCGTCACCG | CCCCGGGTGC | TACCCGATGT | GTCTGGCCCA | GTGCACTAAG | GTCTCTCAAT | 840 |
| TTGTCGTTCG | CTGGGCTGGA | GCAAGTGCCT | AAGGGACTGC | CCCCTAAGCT | CAGCGTGCTT | 900 |
| GATCTCAGCT | GCAACAAGCT | AAGCAGGGAG | CCGCGGCGAG | ACGAGCTGCC | CGAGGTAAAT | 960 |
| GACCTGACTC | TGGACGGAAA | TCCCTTTCTG | GACCCTGGAG | CCCTCCAGCA | CCAAAATGAC | 1020 |
| CCGATGATCT | CCGGCGTGGT | CCCAGCCTGT | GCGCGTTCTG | CCTTGACCAT | GGGGGTGTCA | 1080 |
| GGAGCCCTGG | CGCTGCTTCA | AGGAGCCCGA | GGCTTCGCGT | AA | | 1122 |

(2) INFORMATION FOR SEQ ID NO: 2:

(i) SEQUENCE CHARACTERISTICS:
        (A) LENGTH: 1128 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

| | | | | | |
|---|---|---|---|---|---|
| ATGGAGCGCG | CGTCCTGCTT | GTTGCTGCTG | CTGCTGCCGC | TGGTGCACGT | CTCTGCGACC | 60 |
| ACGCCAGAAC | CTTGTGAGCT | GGACGATGAA | GATTTCCGCT | GCGTCTGCAA | CTTCTCCGAA | 120 |
| CCTCAGCCCC | ACTGGTCCGA | AGCCTTCCAG | TGTGTGTCTG | CAGTAGAGGT | GGAGATCCAT | 180 |
| GCCGGCGGTC | TCAACCTAGA | GCCGTTTCTA | AAGCGCGTCG | ATGCGGACGC | CGACCCGCGG | 240 |
| CAGTATGCTG | ACACGGTCAA | GGCTCTCCGC | GTGCGGCGGC | TCACAGTGGG | AGCCGCACAG | 300 |
| GTTCCTGCTC | AGCTACTGGT | AGGCGCCCTG | CGTGTGCTAG | CGTACTCCCG | CCTCAAGGAA | 360 |
| CTGACGCTCG | AGGACCTAAA | GATAACCGGC | ACCATGCCTC | CGCTGCCTCT | GGAAGCCACA | 420 |
| GGACTTGCAC | TTTCCAGCTT | GCGCCTACGC | AACGTGTCGT | GGGCGACAGG | GCGTTCTTGG | 480 |
| CTCGCCGAGC | TGCAGCAGTG | GCTCAAGCCA | GGCCTCAAGG | TACTGAGCAT | GCCCAAGCA | 540 |
| CACTCGCCTG | CCTTTTCCTG | CGAACAGGTT | CGCGCCTTCC | CGGCCCTTAC | CAGCCTAGAC | 600 |
| CTGTCTGACA | ATCCTGGACT | GGGCGAACGC | GGACTGATGG | CGGCTCTCTG | TCCCCACAAG | 660 |
| TTCCCGGCCA | TCCAGAATCT | AGCGCTGCGC | AACACAGGAA | TGGAGACGCC | CACAGGCGTG | 720 |
| TGCGCCGCAC | TGGCGGCGGC | AGGTGTGCAG | CCCCACAGCC | TAGACCTCAG | CCACAACTCG | 780 |

| | | |
|---|---|---|
| CTGCGCGCCA CCGTAAACCC TAGCGCTCCG AGATGCATGT GGTCCAGCGC CCTGAACTCC | 840 |
| CTCAATCTGT CGTTCGCTGG GCTGGAACAG GTGCCTAAAG GACTGCCAGC CAAGCTCAGA | 900 |
| GTGCTCGATC TCAGCTGCAA CAGACTGAAC AGGGCGCCGC AGCCTGACGA GCTGCCCGAG | 960 |
| GTGGATAACC TGACACTGGA CGGGAATCCC TTCCTGGTCC CTGGAACTGC CCTCCCCCAC | 1020 |
| GAGGGCTCAA TGAACTCCGG CGTGGTCCCA GCCTGTGCAC GTTCGACCCT GTCGGTGGGG | 1080 |
| GTGTCGGGAA CCCTGGTGCT GCTCCAAGGG GCCCGGGGCT TTGCCTAA | 1128 |

(2) INFORMATION FOR SEQ ID NO: 3:

(i) SEQUENCE CHARACTERISTICS:
        (A) LENGTH: 1101 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

| | | |
|---|---|---|
| ATGGAGCGTG TGCTTGGCTT GTTGCTGTTG CTTCTGGTGC ACGCCTCTCC CGCCCCACCA | 60 |
| GAGCCCTGCG AGCTAGACGA GGAAAGTTGT TCCTGCAACT TCTCAGATCC GAAGCCAGAT | 120 |
| TGGTCCAGCG CTTTCAATTG TTTGGGGGCG GCAGATGTGG AATTGTACGG CGGCGGCCGC | 180 |
| AGCCTGGAAT ACCTTCTAAA GCGTGTGGAC ACGGAAGCAG ATCTGGGGCA GTTCACTGAT | 240 |
| ATTATCAAGT CTCTGTCCTT AAAGCGGCTT ACGGTGCGGG CCGCGCGGAT TCCTAGTCGG | 300 |
| ATTCTATTCG GAGCCCTGCG TGTGCTCGGG ATTTCCGGCC TCCAGGAACT GACTCTTGAA | 360 |
| AATCTCGAGG TAACCGGCAC CGCGCCGCCA CCGCTTCTGG AAGCCACCGG ACCCGATCTC | 420 |
| AACATCTTGA ACCTCCGCAA CGTGTCGTGG GCAACAAGGG ATGCCTGGCT CGCAGAACTG | 480 |
| CAGCAGTGGC TAAAGCCTGG ACTCAAGGTA CTGAGTATTG CCCAAGCACA CTCACTCAAC | 540 |
| TTTTCCTGCG AACAGGTCCG CGTCTTCCCT GCCCTCTCCA CCTTAGACCT GTCTGACAAT | 600 |
| CCTGAATTGG GCGAGAGAGG ACTGATCTCA GCCCTCTGTC CCCTCAAGTT CCCGACCCTC | 660 |
| CAAGTTTTAG CGCTGCGTAA CGCGGGGATG GAGACGCCCA GCGGCGTGTG CTCTGCGCTG | 720 |
| GCCGCAGCAA GGGTACAGCT GCAAGGACTA GACCTTAGTC ACAATTCACT GCGGGATGCT | 780 |
| GCAGGCGCTC CGAGTTGTGA CTGGCCCAGT CAGCTAAACT CGCTCAATCT GTCTTTCACT | 840 |
| GGGCTGAAGC AGGTACCTAA AGGGCTGCCA GCCAAGCTCA GCGTGCTGGA TCTCAGTTAC | 900 |
| AACAGGCTGG ATAGGAACCC TAGCCCAGAT GAGCTGCCCC AAGTGGGGAA CCTGTCACTT | 960 |
| AAAGGAAATC CCTTTTTGGA CTCTGAATCC CACTCGGAGA AGTTTAACTC TGGCGTAGTC | 1020 |
| ACCGCCGGAG CTCCATCATC CCAAGCAGTG GCCTTGTCAG GAACTCTGGC TTTGCTCCTA | 1080 |
| GGAGATCGCC TCTTTGTTTA A | 1101 |

(2) INFORMATION FOR SEQ ID NO: 4:

(i) SEQUENCE CHARACTERISTICS:
        (A) LENGTH: 373 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 4:

```
Met Val Cys Val Pro Tyr Leu Leu Leu Leu Leu Pro Ser Leu Leu
 1               5                  10                  15
```

```
Arg Val Ser Ala Asp Thr Thr Glu Pro Cys Glu Leu Asp Asp Asp
            20                  25                  30

Phe Arg Cys Val Cys Asn Phe Thr Asp Pro Lys Pro Asp Trp Ser Ser
        35                  40                  45

Ala Val Gln Cys Met Val Ala Val Glu Val Glu Ile Ser Ala Gly Gly
    50                  55                  60

Arg Ser Leu Glu Gln Phe Leu Lys Gly Ala Asp Thr Asn Pro Lys Gln
65                  70                  75                  80

Tyr Ala Asp Thr Ile Lys Ala Leu Arg Val Arg Arg Leu Lys Leu Gly
                85                  90                  95

Ala Ala Gln Val Pro Ala Gln Leu Leu Val Ala Val Leu Arg Ala Leu
            100                 105                 110

Gly Tyr Ser Arg Leu Lys Glu Leu Thr Leu Glu Asp Leu Glu Val Thr
        115                 120                 125

Gly Pro Thr Pro Pro Thr Pro Leu Glu Ala Ala Gly Pro Ala Leu Thr
    130                 135                 140

Thr Leu Ser Leu Arg Asn Val Ser Trp Thr Thr Gly Ala Trp Leu
145                 150                 155                 160

Gly Glu Leu Gln Gln Trp Leu Lys Pro Gly Leu Arg Val Leu Asn Ile
                165                 170                 175

Ala Gln Ala His Ser Leu Ala Phe Pro Cys Ala Gly Leu Ser Thr Phe
            180                 185                 190

Glu Ala Leu Thr Thr Leu Asp Leu Ser Asp Asn Pro Ser Leu Gly Asp
        195                 200                 205

Thr Gly Leu Met Ala Ala Leu Cys Pro Asn Lys Phe Pro Ala Leu Gln
    210                 215                 220

Tyr Leu Ala Leu Arg Asn Ala Gly Met Glu Thr Pro Ser Gly Val Cys
225                 230                 235                 240

Ala Ala Leu Ala Ala Arg Val Gln Pro Gln Ser Leu Asp Leu Ser
                245                 250                 255

His Asn Ser Leu Arg Val Thr Ala Pro Gly Ala Thr Arg Cys Val Trp
            260                 265                 270

Pro Ser Ala Leu Arg Ser Leu Asn Leu Ser Phe Ala Gly Leu Glu Gln
        275                 280                 285

Val Pro Lys Gly Leu Pro Pro Lys Leu Ser Val Leu Asp Leu Ser Cys
    290                 295                 300

Asn Lys Leu Ser Arg Glu Pro Arg Arg Asp Glu Leu Pro Glu Val Asn
305                 310                 315                 320

Asp Leu Thr Leu Asp Gly Asn Pro Phe Leu Asp Pro Gly Ala Leu Gln
                325                 330                 335

His Gln Asn Asp Pro Met Ile Ser Gly Val Val Pro Ala Cys Ala Arg
            340                 345                 350

Ser Ala Leu Thr Met Gly Val Ser Gly Ala Leu Ala Leu Gln Gly
        355                 360                 365

Ala Arg Gly Phe Ala
    370
```

(2) INFORMATION FOR SEQ ID NO: 5:

(i) SEQUENCE CHARACTERISTICS:
        (A) LENGTH: 375 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 5:

```
Met Glu Arg Ala Ser Cys Leu Leu Leu Leu Pro Leu Val His
1               5                   10                  15

Val Ser Ala Thr Thr Pro Glu Pro Cys Glu Leu Asp Asp Glu Asp Phe
            20                  25                  30

Arg Cys Val Cys Asn Phe Ser Glu Pro Gln Pro Asp Trp Ser Glu Ala
                35                  40                  45

Phe Gln Cys Val Ser Ala Val Glu Val Glu Ile His Ala Gly Gly Leu
    50                  55                  60

Asn Leu Glu Pro Phe Leu Lys Arg Val Asp Ala Asp Ala Asp Pro Arg
65                  70                  75                  80

Gln Tyr Ala Asp Thr Val Lys Ala Leu Arg Val Arg Arg Leu Thr Val
                85                  90                  95

Gly Ala Ala Gln Val Pro Ala Gln Leu Leu Val Gly Ala Leu Arg Val
                100                 105                 110

Leu Ala Tyr Ser Arg Leu Lys Glu Leu Thr Leu Glu Asp Leu Lys Ile
            115                 120                 125

Thr Gly Thr Met Pro Pro Leu Pro Leu Glu Ala Thr Gly Leu Ala Leu
130                 135                 140

Ser Ser Leu Arg Leu Arg Asn Val Ser Trp Ala Thr Gly Arg Ser Trp
145                 150                 155                 160

Leu Ala Glu Leu Gln Gln Trp Leu Lys Pro Gly Leu Lys Val Leu Ser
                165                 170                 175

Ile Ala Gln Ala His Ser Pro Ala Phe Ser Tyr Glu Gln Val Arg Ala
            180                 185                 190

Phe Pro Ala Leu Thr Ser Leu Asp Leu Ser Asp Asn Pro Gly Leu Gly
        195                 200                 205

Glu Arg Gly Leu Met Ala Ala Leu Cys Pro His Lys Phe Pro Ala Ile
    210                 215                 220

Gln Asn Leu Ala Leu Arg Asn Thr Gly Met Glu Thr Pro Thr Gly Val
225                 230                 235                 240

Cys Ala Ala Leu Ala Ala Ala Gly Val Gln Pro His Ser Leu Asp Leu
                245                 250                 255

Ser His Asn Ser Leu Arg Ala Thr Val Asn Pro Ser Ala Pro Arg Cys
            260                 265                 270

Met Trp Ser Ser Ala Leu Asn Ser Leu Asn Leu Ser Phe Ala Gly Leu
        275                 280                 285

Glu Gln Val Pro Lys Gly Leu Pro Ala Lys Leu Arg Val Leu Asp Leu
    290                 295                 300

Ser Cys Asn Arg Leu Asn Arg Ala Pro Gln Pro Asp Glu Leu Pro Glu
305                 310                 315                 320

Val Asp Asn Leu Thr Leu Asp Gly Asn Pro Phe Leu Val Pro Gly Thr
                325                 330                 335

Ala Leu Pro His Glu Gly Ser Met Asn Ser Gly Val Val Pro Ala Cys
            340                 345                 350

Ala Arg Ser Thr Leu Ser Val Gly Val Ser Gly Thr Leu Val Leu Leu
        355                 360                 365

Gln Gly Ala Arg Gly Phe Ala
370                 375
```

(2) INFORMATION FOR SEQ ID NO: 6:

```
    (i) SEQUENCE CHARACTERISTICS:
        (A) LENGTH: 366 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO: 6:

Met Glu Arg Val Leu Gly Leu Leu Leu Leu Leu Val His Ala Ser
1               5                   10                  15

Pro Ala Pro Glu Pro Cys Glu Leu Asp Glu Ser Cys Ser Cys
                20                  25                  30

Asn Phe Ser Asp Pro Lys Pro Asp Trp Ser Ser Ala Phe Asn Cys Leu
            35                  40                  45

Gly Ala Ala Asp Val Glu Leu Tyr Gly Gly Arg Ser Leu Glu Tyr
50                  55                  60

Leu Leu Lys Arg Val Asp Thr Glu Ala Asp Leu Gly Gln Phe Thr Asp
65                  70                  75                  80

Ile Ile Lys Ser Leu Ser Leu Lys Arg Leu Thr Val Arg Ala Ala Arg
                85                  90                  95

Ile Pro Ser Arg Ile Leu Phe Gly Ala Leu Arg Val Leu Gly Ile Ser
                100                 105                 110

Gly Leu Gln Glu Leu Thr Leu Glu Asn Leu Glu Val Thr Gly Thr Ala
                115                 120                 125

Pro Pro Pro Leu Leu Glu Ala Thr Gly Pro Asp Leu Asn Ile Leu Asn
                130                 135                 140

Leu Arg Asn Val Ser Trp Ala Thr Arg Asp Ala Trp Leu Ala Glu Leu
145                 150                 155                 160

Gln Gln Trp Leu Lys Pro Gly Leu Lys Val Leu Ser Ile Ala Gln Ala
                165                 170                 175

His Ser Leu Asn Phe Ser Cys Glu Gln Val Arg Val Phe Pro Ala Leu
                180                 185                 190

Ser Thr Leu Asp Leu Ser Asp Asn Pro Glu Leu Gly Glu Arg Gly Leu
                195                 200                 205

Ile Ser Ala Leu Cys Pro Leu Lys Phe Pro Thr Leu Gln Val Leu Ala
                210                 215                 220

Leu Arg Asn Ala Gly Met Glu Thr Pro Ser Gly Val Cys Ser Ala Leu
225                 230                 235                 240

Ala Ala Ala Arg Val Gln Leu Gln Gly Leu Asp Leu Ser His Asn Ser
                245                 250                 255

Leu Arg Asp Ala Ala Gly Ala Pro Ser Cys Asp Trp Pro Ser Gln Leu
                260                 265                 270

Asn Ser Leu Asn Leu Ser Phe Thr Gly Leu Lys Gln Val Pro Lys Gly
                275                 280                 285

Leu Pro Ala Lys Leu Ser Val Leu Asp Leu Ser Tyr Asn Arg Leu Asp
                290                 295                 300

Arg Asn Pro Ser Pro Asp Glu Leu Pro Gln Val Gly Asn Leu Ser Leu
305                 310                 315                 320

Lys Gly Asn Pro Phe Leu Asp Ser Glu Ser His Ser Glu Lys Phe Asn
                325                 330                 335

Ser Gly Val Val Thr Ala Gly Ala Pro Ser Ser Gln Ala Val Ala Leu
                340                 345                 350

Ser Gly Thr Leu Ala Leu Leu Leu Gly Asp Arg Leu Phe Val
                355                 360                 365
```

(2) INFORMATION FOR SEQ ID NO: 7:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Oligonucleotide"

(xi) SEQUENCE DESCRIPTION: SEQ ID NO: 7:

GCTAGCGCTA GCCACCATGG TGTGCGTGCC CTACCTGCT                         39

(2) INFORMATION FOR SEQ ID NO: 8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Oligonucleotide"

(xi) SEQUENCE DESCRIPTION: SEQ ID NO: 8:

GCTAGCGCTA GCCGCGAAGC CTCGGGCTCC TTGAAG                           36

(2) INFORMATION FOR SEQ ID NO: 9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Oligonucleotide"

(xi) SEQUENCE DESCRIPTION: SEQ ID NO: 9:

CTCGAGCTCG AGGCTAGCCA CCATGGTGTG CGTGCC                           36

(2) INFORMATION FOR SEQ ID NO: 10:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Oligonucleotide"

(xi) SEQUENCE DESCRIPTION: SEQ ID NO: 10:

CTCGAGCTGA GGGATCCCTA AGCGTAATCT GGAAC                             35

(2) INFORMATION FOR SEQ ID NO: 11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Oligonucleotide"

(xi) SEQUENCE DESCRIPTION: SEQ ID NO: 11:

CTAGAATTCT CTCCCGCCCC ACCAGAGCCC TGCG                               34

(2) INFORMATION FOR SEQ ID NO: 12:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Oligonucleotide"

(xi) SEQUENCE DESCRIPTION: SEQ ID NO: 12:

CTAGAATTCT TAAACAAAGA GGCGATCTCC TAGG                       34

(2) INFORMATION FOR SEQ ID NO: 13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Oligonucleotide"

(xi) SEQUENCE DESCRIPTION: SEQ ID NO: 13:

TACCAATACG ATGTTCCAGA TTACGCTTAG                              30

(2) INFORMATION FOR SEQ ID NO: 14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Olgonucleotide"

(xi) SEQUENCE DESCRIPTION: SEQ ID NO: 14:

GCAGTCGACA CTATAGAATA CTCAAGC                                 27

(2) INFORMATION FOR SEQ ID NO: 15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic Oligonucleotide"

(xi) SEQUENCE DESCRIPTION: SEQ ID NO: 15:

TTCGTCGACA TTGGGCCCTC TAGA                                     24